(12) United States Patent
Tal et al.

(10) Patent No.: US 12,661,124 B2
(45) Date of Patent: Jun. 23, 2026

(54) LONGITUDINALLY COMPRESSIBLE VASCULAR OCCLUDER

(71) Applicant: VenaCore Inc., Tel-Aviv (IL)

(72) Inventors: Michael Gabriel Tal, Tel Aviv (IL); Navot Rabban, Ramat-Gan (IL); Amit Greener, Tel-Aviv (IL)

(73) Assignee: ToTal Medical Inc., Wilmington, DE (US)

( * ) Notice: Subject to any disclaimer, the term of this patent is extended or adjusted under 35 U.S.C. 154(b) by 435 days.

(21) Appl. No.: 18/023,624

(22) PCT Filed: Aug. 30, 2021

(86) PCT No.: PCT/US2021/048194
§ 371 (c)(1),
(2) Date: Feb. 27, 2023

(87) PCT Pub. No.: WO2022/051215
PCT Pub. Date: Mar. 10, 2022

(65) Prior Publication Data
US 2024/0090902 A1     Mar. 21, 2024

Related U.S. Application Data

(60) Provisional application No. 63/109,650, filed on Nov. 4, 2020, provisional application No. 63/073,055, filed on Sep. 1, 2020.

(51) Int. Cl.
A61B 17/12 (2006.01)
A61B 17/00 (2006.01)

(52) U.S. Cl.
CPC .. A61B 17/12172 (2013.01); A61B 17/12031 (2013.01); A61B 17/12036 (2013.01);
(Continued)

(58) Field of Classification Search
CPC ........ A61B 17/12172; A61B 17/12031; A61B 17/12036; A61B 17/12109;
(Continued)

(56) References Cited

U.S. PATENT DOCUMENTS 3,834,394 A   9/1974   Hunter et al.
4,517,979 A   5/1985   Pecenka
(Continued)

FOREIGN PATENT DOCUMENTS

EP       3456272 A1    3/2019
WO    2016010812 A1    1/2016
(Continued)

OTHER PUBLICATIONS

International Search Report and Written Opinion mailed Dec. 17, 2021 in PCT/US2021/048194.
(Continued)

*Primary Examiner* — Richard G Louis
(74) *Attorney, Agent, or Firm* — Veros Legal Solutions, LLP

(57)     ABSTRACT

Vascular occluder and methods for occluding a passage are provided. The vascular occluder comprises an elongated occluder body with an occluding section, and a tension member connected with one end thereof to occluder body. Occluding section forms a tubular bellows-like shaped structure comprising a plurality of bellows sections when in an elastically relaxed configuration, is elastically stretchable longitudinally from the elastically relaxed configuration to a delivery configuration, and elastically compressible longitudinally from the elastically relaxed configuration, by way of applying tension to the tension member, to a fixed deployed configuration.

9 Claims, 16 Drawing Sheets

(52) U.S. Cl.
CPC ................... *A61B 17/12109* (2013.01); *A61B 2017/00592* (2013.01); *A61B 2017/00862* (2013.01); *A61B 2017/12054* (2013.01)

(58) Field of Classification Search
CPC ........... A61B 2017/00592; A61B 2017/00862; A61B 2017/12054; A61B 2017/00243; A61B 2017/00597; A61B 2017/00606; A61B 2017/00619; A61B 2017/00623; A61B 2017/1205; A61B 17/0057; A61B 17/12113; A61B 17/12163; A61B 17/12177

See application file for complete search history.

(56) References Cited

U.S. PATENT DOCUMENTS

| | | | |
|---|---|---|---|
| 4,832,055 | A | 5/1989 | Palestrant |
| 5,192,301 | A | 3/1993 | Kamiya et al. |
| 5,217,484 | A | 6/1993 | Marks |
| 5,304,195 | A | 4/1994 | Twyford, Jr. et al. |
| 5,350,397 | A | 9/1994 | Palermo et al. |
| 5,383,926 | A | 1/1995 | Lock et al. |
| 5,725,552 | A | 3/1998 | Kotula et al. |
| 5,824,046 | A | 10/1998 | Smith et al. |
| 5,895,391 | A | 4/1999 | Farnholtz |
| 5,954,765 | A | 9/1999 | Ruiz |
| 6,336,937 | B1 | 1/2002 | Vonesh et al. |
| 6,350,277 | B1 | 2/2002 | Kocur |
| 6,419,686 | B1 | 7/2002 | McLeod et al. |
| 6,589,256 | B2 | 7/2003 | Forber |
| 6,638,293 | B1 | 10/2003 | Makower et al. |
| 6,878,160 | B2 | 4/2005 | Gilligan et al. |
| 6,953,476 | B1 | 10/2005 | Shalev |
| 7,159,593 | B2 | 1/2007 | McCarthy et al. |
| 7,530,995 | B2 | 5/2009 | Quijano et al. |
| 8,105,344 | B2 | 1/2012 | Yeung et al. |
| 8,273,101 | B2 | 9/2012 | Garcia et al. |
| 8,328,860 | B2 | 12/2012 | Strauss et al. |
| 8,398,670 | B2 | 3/2013 | Amplatz et al. |
| 8,425,584 | B2 | 4/2013 | Cully et al. |
| 8,556,954 | B2 | 10/2013 | Muvhar et al. |
| 8,621,975 | B2 | 1/2014 | Russo et al. |
| 8,636,760 | B2 | 1/2014 | Garcia et al. |
| 8,777,979 | B2 | 7/2014 | Shrivastava et al. |
| 8,858,612 | B2 | 10/2014 | Ben-Muvhar et al. |
| 8,906,057 | B2 | 12/2014 | Connor et al. |
| 8,911,489 | B2 | 12/2014 | Ben-Muvhar |
| 8,923,973 | B2 | 12/2014 | Gross |
| 8,984,733 | B2 | 3/2015 | Leopold et al. |
| 9,095,344 | B2 | 8/2015 | Leopold et al. |
| 9,107,743 | B2 | 8/2015 | Iancea et al. |
| 9,289,215 | B2 | 3/2016 | Strauss et al. |
| 9,364,354 | B2 | 6/2016 | Ben-Muvhar et al. |
| 9,402,634 | B2 | 8/2016 | Russo et al. |
| 9,451,965 | B2 | 9/2016 | Rudakov et al. |
| 9,566,419 | B2 | 2/2017 | Frigstad et al. |
| 9,579,104 | B2 | 2/2017 | Beckham et al. |
| 9,636,116 | B2 | 5/2017 | Rudakov et al. |
| 9,681,876 | B2 | 6/2017 | Cragg et al. |
| 9,707,124 | B2 | 7/2017 | Brenzel et al. |
| 9,737,306 | B2 | 8/2017 | Rudakov et al. |
| 9,737,308 | B2 | 8/2017 | Rudakov |
| 9,744,059 | B2 | 8/2017 | Ben-Muvhar |
| 9,814,466 | B2 | 11/2017 | Kadam |
| 9,848,883 | B2 | 12/2017 | Cragg et al. |
| 10,010,328 | B2 | 7/2018 | Cragg et al. |
| 10,178,995 | B2 | 1/2019 | Cragg et al. |
| 10,206,685 | B2 | 2/2019 | Trommeter et al. |
| 10,335,155 | B2 | 7/2019 | Beckham et al. |
| 10,420,563 | B2 | 9/2019 | Hebert et al. |
| 10,441,290 | B2 | 10/2019 | Rudakov et al. |
| 10,548,606 | B2 | 2/2020 | Hui et al. |
| 10,603,043 | B2 | 3/2020 | Barkenbus et al. |
| 2002/0045931 | A1 | 4/2002 | Sogard et al. |
| 2003/0065386 | A1 | 4/2003 | Weadock |
| 2004/0098030 | A1 | 5/2004 | Makower et al. |
| 2004/0230288 | A1 | 11/2004 | Rosenthal |
| 2005/0064009 | A1 | 3/2005 | Bates |
| 2005/0288786 | A1 | 12/2005 | Chanduszko |
| 2006/0106449 | A1 | 5/2006 | Muvhar |
| 2006/0106450 | A1 | 5/2006 | Muvhar |
| 2006/0116627 | A1 | 6/2006 | Bridges et al. |
| 2008/0103522 | A1 | 5/2008 | Steingisser et al. |
| 2008/0249562 | A1* | 10/2008 | Cahill ................ A61B 17/0057 606/215 |
| 2009/0082803 | A1 | 3/2009 | Adams et al. |
| 2010/0094395 | A1* | 4/2010 | Kellett ............... A61B 17/1215 623/1.11 |
| 2012/0078295 | A1 | 3/2012 | Steiner et al. |
| 2012/0316597 | A1 | 12/2012 | Fitz et al. |
| 2014/0052103 | A1 | 2/2014 | Cully et al. |
| 2014/0121759 | A1 | 5/2014 | Cully |
| 2015/0005809 | A1 | 1/2015 | Ayres et al. |
| 2015/0133989 | A1 | 5/2015 | Lubock et al. |
| 2015/0173919 | A1 | 6/2015 | Baldwin |
| 2015/0282958 | A1 | 10/2015 | Centola et al. |
| 2016/0228125 | A1 | 8/2016 | Pederson, Jr. et al. |
| 2016/0256169 | A1 | 9/2016 | Ben-Muvhar et al. |
| 2016/0317135 | A1 | 11/2016 | Glimsdale et al. |
| 2016/0345979 | A1 | 12/2016 | Adams et al. |
| 2017/0086854 | A1 | 3/2017 | Cragg et al. |
| 2017/0165059 | A1 | 6/2017 | Roselli et al. |
| 2017/0172771 | A1 | 6/2017 | Bruckheimer et al. |
| 2017/0354421 | A1 | 12/2017 | Maguire et al. |
| 2017/0367713 | A1 | 12/2017 | Greene, Jr. et al. |
| 2018/0085128 | A1 | 3/2018 | Bellomo et al. |
| 2018/0242980 | A1 | 8/2018 | Lubock et al. |
| 2018/0303639 | A1 | 10/2018 | Ben-Muvhar |
| 2019/0126014 | A1 | 5/2019 | Kapur et al. |
| 2019/0133601 | A1 | 5/2019 | Cragg et al. |
| 2019/0255302 | A1 | 8/2019 | Kapur et al. |
| 2020/0275935 | A1* | 9/2020 | Maisano .......... A61B 17/12122 |
| 2021/0121183 | A1 | 4/2021 | Sharma |
| 2021/0386429 | A1 | 12/2021 | Franano et al. |

FOREIGN PATENT DOCUMENTS

| | | |
|---|---|---|
| WO | 2017062572 A1 | 4/2017 |
| WO | 2017062740 A1 | 4/2017 |
| WO | 2017214577 A1 | 12/2017 |
| WO | 2018197983 A1 | 11/2018 |
| WO | 2018225059 A1 | 12/2018 |
| WO | 2019057950 A1 | 3/2019 |
| WO | 2019083989 A1 | 5/2019 |

OTHER PUBLICATIONS

International Search Report and Written Opinion mailed May 6, 2022 in PCT/US2022/016632.
Extended European Search Report mailed on Jul. 26, 2024 in EP 21864947.3.

* cited by examiner

DISTAL                                              PROXIMAL

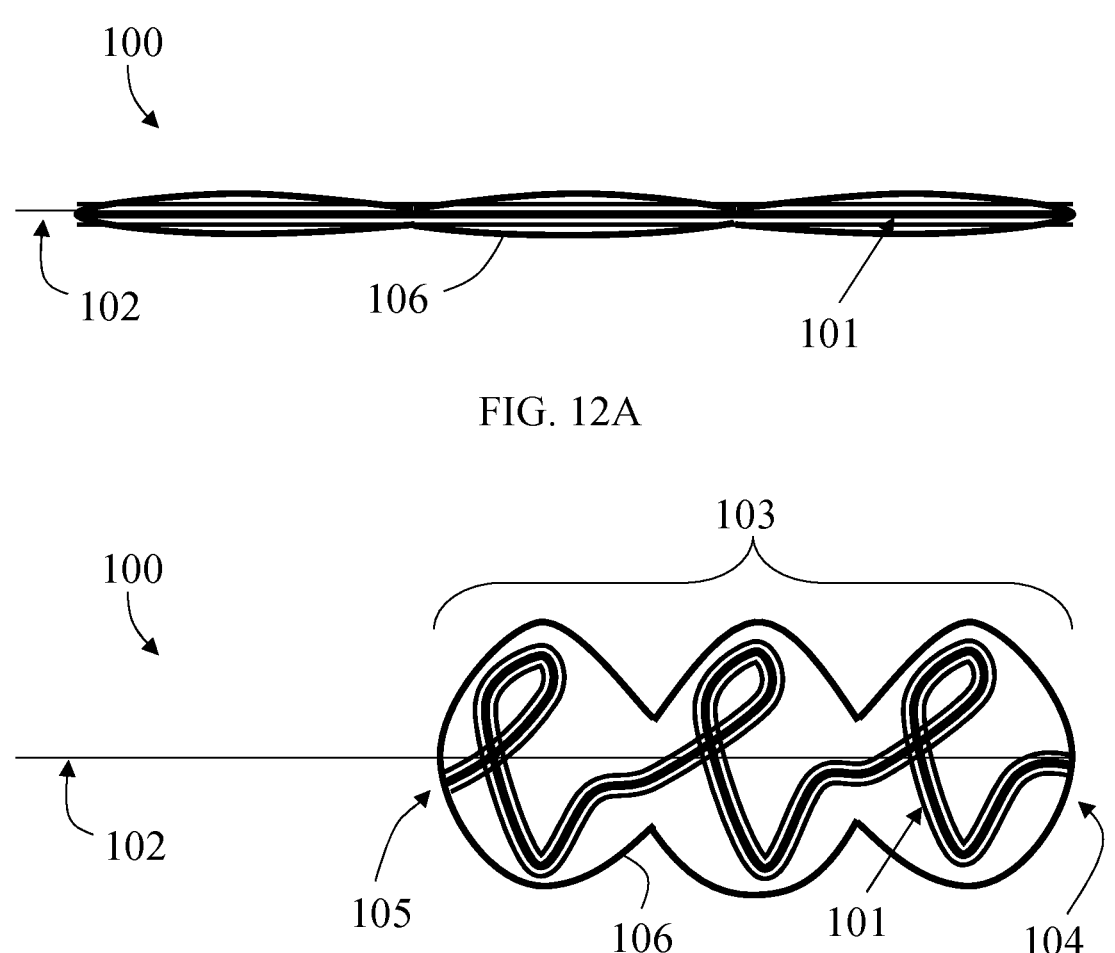
FIG. 12A
FIG. 12B
FIG. 12C

100

LONGITUDINALLY COMPRESSIBLE VASCULAR OCCLUDER

FIELD OF THE INVENTION

The present disclosure relates to devices and methods for treating a target blood vessel, and more particularly, but not exclusively, to vascular occluders and methods for occluding target blood vessels such as arteries.

BACKGROUND OF THE INVENTION

Some medical procedures, such as embolization, involve occluding a blood vessel for reducing pressure on aneurysms, restricting a hemorrhage, or diminishing blood supply to tumors or growths in the body. Vascular plugs are type of mechanical embolization devices commonly used for occluding a targeted portion of vein or artery with a relatively low-profile delivery and can be released in a controlled fashion. Most common are the Amplatzer Vascular Plugs (by Abbott Laboratories, Inc.; Illinois, USA) that have been used for the embolization of medium to large vascular vessels (e.g., greater than 5 mm or greater than 10 mm, respectively) by extending along a relatively long portion of the target vessel, usually greater than 5 mm in length.

In recent years there is a growing trend of micro sized vascular plugs designed for microcatheter delivery, for example the MVP Micro Vascular Plug series (by Medtronic, Plc.; Dublin, Ireland), that include smaller sized vascular plugs deliverable via small-diameter microcatheters but capable of treating vessels smaller than 5 mm in diameter, and vascular plugs of greater size which require relatively large-diameter microcatheters (4 Fr OD or more) for treating vessels greater than 5 mm in diameter.

There is still an unmet need for mechanical embolization devices (e.g., vascular plugs) capable of meeting three main challenges: (a) blocking high flow rate arteries by applying greater pressure to vessel wall to prevent downstream migration, (b) delivery via catheters smaller in diameter (e.g., microcatheter) for treating a greater range of vessels sizes, such as between 1.5 mm and 20 mm, and (c) increased flexibility for delivering lager-sized vascular plugs in smaller-sized catheters.

SUMMARY OF THE INVENTION

The present disclosure relates to devices and methods for treating a target blood vessel, and more particularly, but not exclusively, to vascular occluders and methods for occluding target blood vessels such as arteries.

In certain embodiments, there is provided a vascular occluder comprising: an elongated occluder body comprising a distal body end, a proximal body end and an occluding section extending along a longitudinal axis between the distal body end and the proximal body end; and a tension member connected with one end thereof to the elongated occluder body.

In some embodiments, the occluding section forms a tubular bellows-like shaped structure comprising a plurality of bellows sections when in an elastically relaxed configuration, and is elastically stretchable longitudinally from the elastically relaxed configuration to a delivery configuration having a delivery length and a delivery diameter, and elastically compressible longitudinally from the elastically relaxed configuration, by way of applying tension to the tension member, to a fixed deployed configuration having a deployed length smaller than the delivery length and a deployed diameter greater than the delivery diameter.

In some embodiments, the vascular occluder is configured such that the occluding section is locks or fixated at the deployed length and/or diameter after having been compressed longitudinally to the deployed configuration.

In some embodiments, the occluding section is configured to lock in the deployed configuration when at least one of the bellows sections is held bent towards the longitudinal axis, towards the proximal body end or towards the distal body end, or when at least one of the bellows sections is held deformed such that a radially outer portion thereof is bent towards the longitudinal axis.

In some embodiments, the vascular occluder comprising a length securing member configured to lock the occluding section, selectively or automatically, in the deployed configuration by preventing or resisting elongation of the occluding section from the deployed length and/or loosening of the tension member, such as by engaging with the taut tension member.

In some embodiments, the tension member extends along the occluding section and connected with a distal end thereof to a distal end of the occluding section or to the distal body end.

In some embodiments, the occluding section includes a plurality of flow obstruction portions provided sequentially along a portion of the tension member and extending at least partially transversely thereto, the tension member passes through a respective lumen of each one of the flow obstruction portions such that one or more of the plurality of flow obstruction portions is movable axially over the tension member relative to remainder of the flow obstruction portions.

In some embodiments, the tension member is connectable or lockable to the occluder body remotely to the first end of the tension member, when in the deployed configuration, for preventing or resisting elongation of the occluding section from the deployed length.

In some embodiments, the tension member is configured to separate or cut to a predetermined length, selectively or automatically, optionally when the tension member is drawn taut to over a predetermined tension threshold and/or when the occluding section is compressed to a predetermined size threshold.

In some embodiments, the occluding section is configured to increase in maximal outer diameter and/or to increase in elastic resistance to radial compression when compressing longitudinally to the deployed configuration from a less elastically stressed longitudinally compressed state.

In some embodiments, at least one of the plurality of bellows sections extends between respective first and second inward creases and comprises: a respective frustum-shaped ascending portion extending from the respective first inward crease to a respective outward crease, and a respective frustum-shaped descending portion, extending from the respective outward crease to the respective second inward crease.

In some embodiments, the at least one of the plurality of bellows sections is less permeable adjacent to the respective first inward crease, second inward crease and/or outward crease than to remainder of the respective frustum-shaped ascending portion and/or frustum-shaped descending portion, to blood flow passing therethrough along the longitudinal axis.

In some embodiments, the at least one of the respective frustum-shaped ascending portion and the frustum-shaped descending portion is configured to reduce blood flow permeability therethrough along the longitudinal axis, when the occluding section changes to the deployed configuration.

In some embodiments, in each pair of adjacent bellows sections comprising of respective first and second bellows sections, the respective second inward crease of the respective first bellows section and the respective first inward crease of the second bellows section are adjoined circumferentially at a mutual curved or bent circumferential inner edge having an inward apex projecting radially-inwardly towards the longitudinal axis.

In some embodiments, the plurality of bellows sections includes at least one larger bellows section having the respective outward crease thereof enclosing a largest diameter greater than diameter of the bodily lumen portion, and at least one smaller bellows section having the respective outward crease thereof enclosing a largest diameter equal to or smaller than diameter of the bodily lumen portion.

In some embodiments, the vascular occluder is configured such that, when the occluding section is in the deployed configuration, the at least one smaller bellows section presses radially outwardly against the larger bellows section.

In some embodiments, at least some of the plurality of bellows sections vary in slant length of the respective frustum-shaped ascending portion and/or frustum-shaped descending portion thereof.

In some embodiments, the respective frustum-shaped ascending portion forms an ascending angle with the longitudinal axis and the respective frustum-shaped descending portion forms a descending angle with the longitudinal axis, wherein, when the occluding section is in the elastically relaxed configuration, the ascending angle is smaller than 900 and the descending angle is greater than 90°, and when the occluding section is in the deployed configuration, each one of the ascending angle and the descending angle is either greater or smaller than 90°.

In some embodiments, the occluding section is formed of a meshed, fenestrated, braided, or interwoven sleeve.

In some embodiments, the vascular occluder is configured such that, when the occluding section is in the deployed configuration, radially inner portions of the plurality of bellows sections and/or of distal and proximal body ends are fixedly pressed tight and/or condensed against each other parallel to the longitudinal axis.

In some embodiments, the vascular occluder is configured such that, when the occluding section is in the deployed configuration, radially outer portions of the plurality of bellows sections, spaced radially outwardly from the radially inner portions, are looser than the radially inner portions and/or allowed to shift relative to each other and/or allowed to form gaps therebetween.

In some embodiments, the delivery length is greater than 10 mm and/or the deployed length is smaller than 6 mm, and/or the deployed length is about 50% or less than the delivery length, and/or the delivery diameter is smaller than 1.5 mm and the deployed diameter is greater than 3 mm.

In some embodiments, the vascular occluder further comprising an elongated pusher selectively detachable from the occluder body, the vascular occluder is sized and configured to pass through a lumen of a catheter when the occluding section is in the delivery configuration, by way of advancing the pusher with the occluder body, at least until the occluding section is entirely protruding via a distal opening of the catheter lumen with the pusher and the tension member extending along the catheter lumen and through a proximal opening of the catheter lumen.

In some embodiments, the occluding section is changeable from the delivery configuration to the elastically relaxed configuration when entirely protruding via the distal catheter opening, when tension in the tension member is below a first predetermined value, and/or the occluding section is changeable from the elastically relaxed configuration to the deployed configuration when tension in the tension member is above a second predetermined value sufficient to compress and lock the occluding section in the deployed configuration.

In some embodiments, the vascular occluder is configured such that the occluding section is less permeable to blood flowing therethrough when in the deployed configuration relative to when in the elastically relaxed configuration.

In some embodiments, the flow obstruction portions are at least partially permeable to blood flowing therethrough, and/or the occluding section includes an impermeable portion configured to substantially reduce or block blood from flowing through the occluding section along the longitudinal axis when in the deployed configuration.

In some embodiments, the impermeable portion includes, or is configured as, a coating of portions of the occluding sections and/or a radially expandable member housed in the occluding section between the flow obstruction portions.

In some embodiments, the impermeable portion includes, or is configured as, an at least one axially extendable-compressible occlusion member extending through the occluding section and configured to allow unhindered stretching of the occluding section to the delivery configuration, and to compress into a flattened or condensed form spanning over most or all axial cross section of the occluding section when in the deployed configuration thereby occluding the occluder body.

In some embodiments, the impermeable portion is configured to allow blood flow through the occluding section when in the elastically relaxed configuration.

In certain embodiments, there is provided a method of occluding a passage in a body of a live subject, the method comprising: inserting a vascular occluder according to claim 1 into or through the passage, while maintaining the occluding section in the delivery configuration; releasing the occluding section in the passage from the delivery configuration such that the occluding section is allowed to shorten and laterally expand into a less elastically stressed configuration; compressing longitudinally the occluding section into the deployed configuration by increasing longitudinal elastic stress of the occluding section relative to the less elastically stressed configuration, thereby occluding the passage; and locking the occluding section in the deployed configuration.

In some embodiments, the compressing includes widening the passage locally with the vascular occluder at least until blood flow rate in the passage reduces by at least 30% of the original blood flow rate.

In some embodiments, the releasing or the compressing longitudinally includes bending at least one of the bellows sections, and the compressing longitudinally or locking includes generating continuous internal stresses configured to hold the at least one of the bellows sections bent, thereby locking the occluding section in the deployed configuration.

In some embodiments, the compressing longitudinally includes applying tension to the tension member, and the locking includes fastening a portion of the tension member to the occluder body remotely to the one end of the tension member for preventing or resisting elongation from the deployed length.

In some embodiments, the method comprising disjoining or cutting the tension member to a predetermined length, optionally by applying tension thereto above a chosen tension force.

In some embodiments, the passage is a blood vessel and the occluding affects immediate or gradual cessation of blood flow through the occluding section in the blood vessel.

In some embodiments, the passage includes an opening in an organ wall separating between distinct organ lumens, wherein the inserting includes passing the occluder body through the opening, and the releasing includes first releasing a distal portion of the occluding section distally to the organ wall and later releasing a proximal portion of the occluding section proximally to the organ wall, such that the compressing occludes the opening.

In some embodiments, the organ wall is a blood vessel wall and the method is configured to treat vessel wall aneurism or a patent ductus arteriosus; or the organ wall is a septal wall and the method is configured to treat a septal defect such as an atrial septal defect.

In some embodiments, the method further comprising: advancing a catheter enclosing a catheter lumen through a blood vessel, such that a distal opening of the catheter lumen is positioned in the passage; and pushing the vascular occluder with a pusher until protruding at least partially the occluding section in the passage via the distal opening.

In some embodiments, the inserting includes the pushing, and/or the compressing includes increasing tension in the tension member sufficiently to compress and lock the occluding section in the deployed configuration.

In some embodiments, the detaching includes releasing the pusher from being rigidly connected to the occluder body, and/or cutting the tension member distally to the pusher.

All technical or/and scientific words, terms, or/and phrases, used herein have the same or similar meaning as commonly understood by one of ordinary skill in the art to which the invention pertains, unless otherwise specifically defined or stated herein. Illustrative embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative description of some embodiments. In this regard, the description taken together with the accompanying drawings make apparent to those skilled in the art how some embodiments may be practiced.

In the drawings.

FIGS. 12A-12C schematically illustrate an exemplary vascular occluder comprising a first exemplary impermeable portion, shown respectively in a delivery configuration, in an elastically relaxed configuration and in a deployed configuration, according to some embodiments;

DETAILED DESCRIPTION

Figures 1A, 1B, 1C:
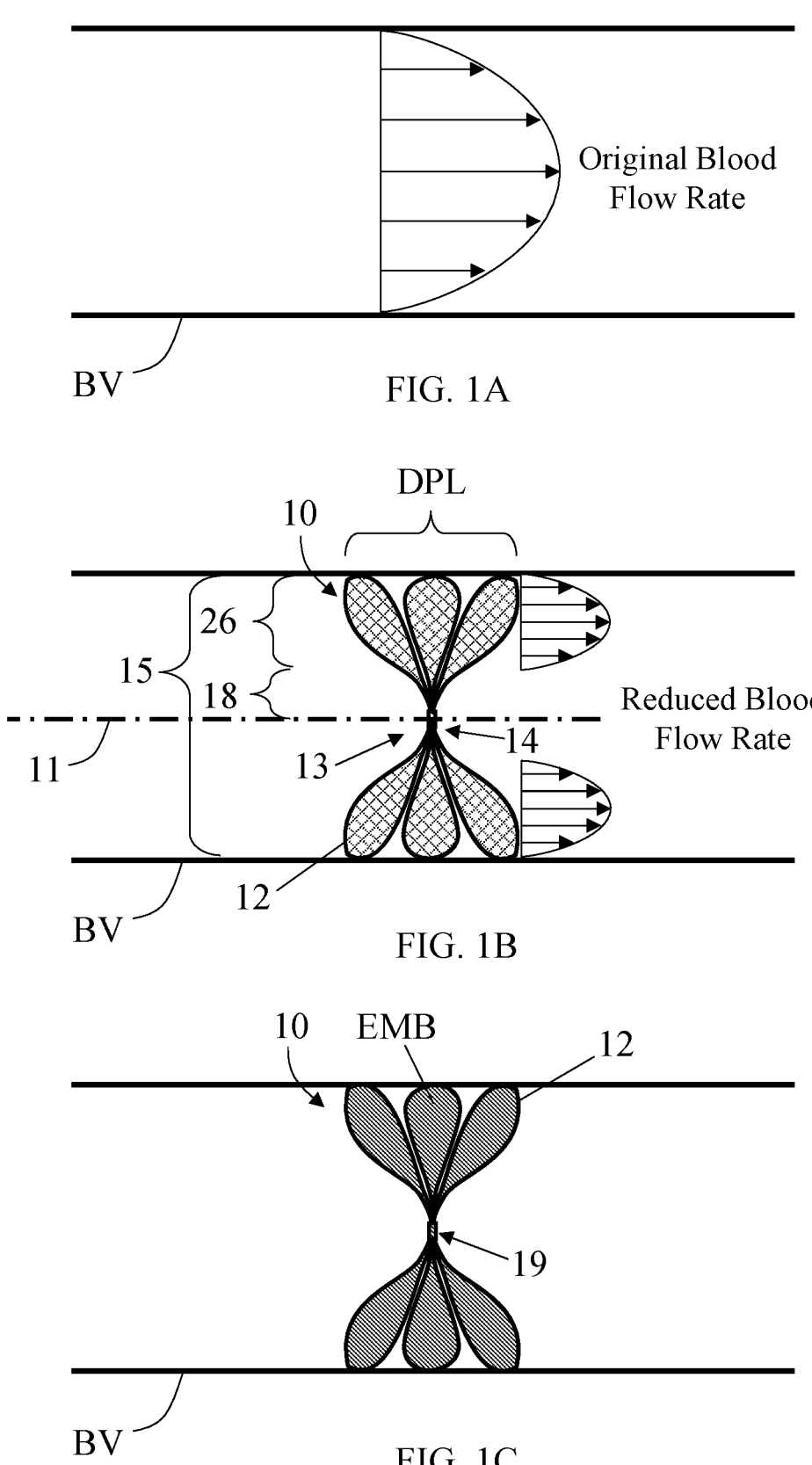
FIGS. 1A-1C schematically illustrate exemplary scenarios representing possible phases of blood flow occlusion following implantation of an exemplary vascular occluder in a target blood vessel, according to some embodiments.

Certain embodiments relate to devices and methods for treating a target blood vessel, and more particularly, but not exclusively, to vascular occluders and methods for occluding target blood vessels such as arteries.

In some embodiments, there is provided a vascular occluder optionally intended for use similarly to a vascular plug or another type of mechanical embolization device. The vascular occluder includes an elongated occluder body optionally formed at least in part from a braided (or otherwise fenestrated, meshed, or woven) sleeve-like structure and is selectively compressible along longitudinal axis thereof from stretched delivery length and form to final compressed deployed length and form. The vascular occluder can be left in a chosen target endoluminal portion of a blood vessel (e.g., artery) when it is fixated in the deployed length.

Compression of the vascular occluder can be performed with and/or via a delivery catheter by optionally using other delivery members such as to eject the vascular occluder and/or to manually compress it in the blood vessel. Compression can be achieved by moving distal and proximal body ends of the occluder body towards each other along the longitudinal axis such as by pressing (e.g., squeezing) internal portion of the distal and/or proximal body end in proximity to the longitudinal axis while allowing peripheral (outer) portions of the distal and/or proximal body end to remain relatively loose and more subjectable to conformity to a shape and/or dimensions imposed by surrounding tissue.

The occluder body may include an occluding section, optionally configured as a bellows-like structure, extending longitudinally between the distal body end and the proximal body end. The bellows-like structure includes a plurality of tubular folds, each fold comprising at least one flow obstructing portion configured to limit or block blood from flowing therethrough. When the occluder body is compressed into the deployed length, the flow obstructing portions extend transversally to the longitudinal axis for obstructing blood flow along the longitudinal axis. Furthermore, the radially inner portions of the folds, which are fixedly pressed tight against each other, are parallel to the longitudinal axis thereby further increasing the obstruction to flow while causing increase in the radial force transferred to the blood vessel wall which anchors the vascular occluder thereto.

In some embodiments, the vascular occluder is fixedly deformable into the compressed deployed length configuration as described, optionally by use of a structural element (e.g., a tension member) configured to lock and/or continuously (e.g., permanently) pull the radially inner portions of the folds and/or distal and proximal body ends of the occluder body towards each other along the longitudinal axis. This structural element may be configured as part of locking mechanism which fastens the radially inner portions together after the operator causes compression therebetween. Optionally, additionally or alternatively, the structural element may be configured as a plastically deformable member (e.g., in a form of one or more plastically deformable wires braided into the occluder body and is mechanically capable of withstanding inner and/or outer stresses optionally acting to re-elongate the occluder body from the compressed length configuration). Optionally, additionally or alternatively, the structural element may be configured as an elastically deformable member optionally connecting between the radially inner portions of the distal and proximal body ends across the folds and being in relaxed or in elastically stretched form when the occluder body is in the compressed length, thereby resisting longitudinal extension and/or causing continuous axial (e.g., pulling) force or stresses therebetween parallel to the longitudinal axis.

The structural and/or functional features described above allow creation of a vascular occluder capable of substantially greater ratios of outer dimensions from stretched delivery length to final compressed length, thereby allowing use of smaller catheters (e.g., microcatheters) with outer diameter of 2.8 Fr or less, for example, for treating small to medium or even large arteries greater than about 5 mm, for example. The use of a structural element, such as a tension member, for locking and/or continuously pulling together radially inner portions of the occluder body's folds and/or proximal and distal body ends, improves anchoring to the blood vessel wall. This allows for diminishing or preventing migration potential by generating increased radially pressure by outward or radially outer portions of the occluder body to the blood vessel wall resulting from the continuous pulling force of structural element on the occluder body radially inner portions. The unique occluder compression presented also facilitates a more focal or accurate placement of the vascular occluder in a smaller length portion of the blood vessel, thereby improving fitting and positioning for different occlusion requirements, which may be considered advantageous in different scenarios for example in cases of arterial raptures or pseudoaneurysms, in which the treatment often requires a focal occlusion of the vessel on both sides of the rapture.

Figures 2A, 2B, 2C:
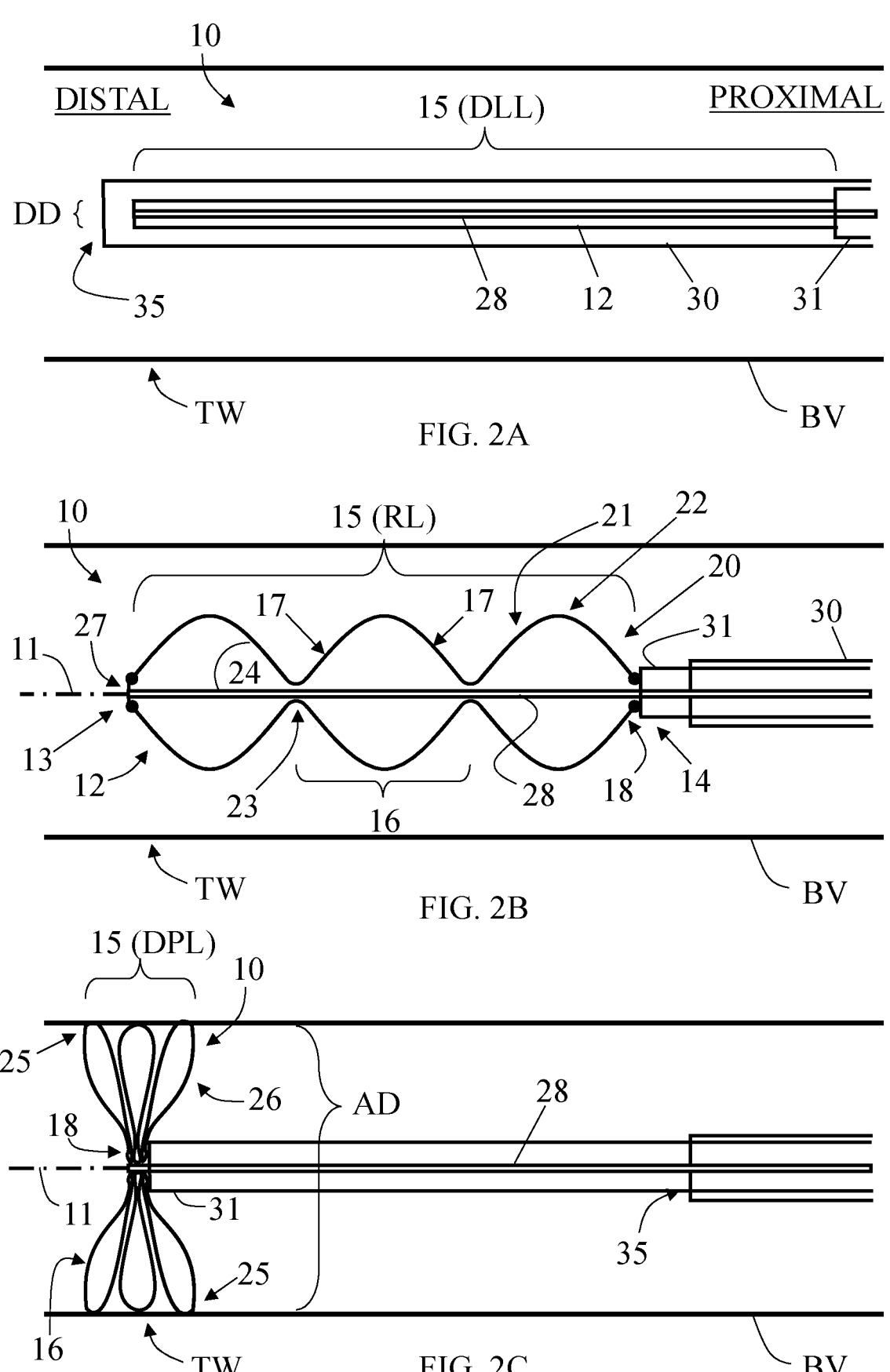
FIGS. 2A-2C schematically illustrate exemplary scenarios representing steps in a first exemplary procedure for implanting the exemplary vascular occluder of FIG. 1B, according to some embodiments.

FIGS. 1A-1C schematically illustrate exemplary scenarios representing possible phases of blood flow occlusion following implantation of an exemplary vascular occluder 10 (shown in a side cross-sectional view) in a target blood vessel BV. FIGS. 2A-2C schematically illustrate exemplary scenarios representing steps in a first exemplary procedure for implanting vascular occluder 10 for occluding blood vessel BV. FIG. 1A shows target blood vessel BV (e.g., artery) before catheter insertion and embolization. FIG. 1B shows same portion of blood vessel BV partially occluded with vascular access port 10 that is in a final compressed deployed length DPL configuration immediately following deployment and catheter withdrawal from the body. FIG. 1C shows same portion of blood vessel BV with vascular occluder 10 following several weeks to months after it had absorbed and/or accumulated emboli EMB sufficiently to diminish substantially or completely block blood flow therethrough.

Vascular occluder 10 as shown has a meshed (e.g., braided) occluder body 12 that is optionally configured also for allowing accumulation of emboli therein and/or in mesh openings thereof, however occluder body 10 may alternatively include, instead or over meshed structure thereof, a fluid tight material (e.g., membrane or coating) fully or partially impermeable to blood flowing therethrough, for causing immediate occlusion once deployed without potentially be depend on naturally-occurring emboli accumulation. Vascular occluder 10 is shown in a symmetric configuration relative to a longitudinal axis 11 thereof for illustrative purpose demonstrating its maintained (e.g., by way of holding or locking) it under a continuous (e.g., permanent) compression particularly across radially inner portions thereof from both ends thereof, however its outward or radially outer portions, located farther to longitudinal axis 11 than the compressed radially inner portions, can be more loose and allowed to deform during or after deployment in same or any other, optionally unsymmetrical, configuration.

Occluder body 12 has generally elongated tubular shape when in a relaxed (i.e., not elastically stressed) length RL, as shown in FIG. 2B for example, and comprises a distal body end 13, a proximal body end 14 and an occluding section 15, that is configured as a bellows-like structure, extending between distal body end 13 and proximal body end 14, and longitudinally compressible along longitudinal axis 11. Vascular occluder 10 also includes a tension member 28 which extends along occluding section 15 and connected with a distal end thereof to distal body end 13 of occluder body 12. Tension member 28 is configured to facilitate selective longitudinal compression of occluding section 15 by causing sufficient tension to tension member 28 while pushing distally a proximal end of occluding section 15 (e.g., by pushing proximal body end 14, as shown in the figures). Occluding section 15 is longitudinally stretchable to delivery length DLL wherein the it is configured to pass unhinderedly through a catheter lumen into target blood vessel BV. Occluding section 15 is also longitudinally compressible to deployed length DPL thereby radially extending with one or more anchoring portions thereof to a deployed diameter DD greater than diameter of the target blood vessel BV, wherein it is configured to limit, filter or block blood from flowing therethrough.

In some embodiments, the deployed length DPL is about 50% or less than the delivery length DLL. In some embodiments, the delivery length DLL (when residing stretched in a catheter, for example) is greater than about 10 mm, optionally greater than about 20 mm, and the deployed length DPL is smaller than about 6 mm, optionally smaller than about 3 mm. The maximal outer diameter of occluding section 15 is smaller than about 2 mm, optionally smaller than about 1.5 mm, when occluding section 15 is in the delivery length DLL and greater than about 3 mm, optionally greater than about 5 mm, when occluder body 12 is in the deployed length DPL. The ratio of maximal outer diameter to length of occluding section 15 is optionally smaller than about 0.05 when occluding section 15 is in the delivery length DLL and greater than about 0.5 when occluder body 12 is in the deployed length DPL.

Occluding section 15 includes a plurality of tubular folds 16, each fold 16 comprising at least one flow obstructing portion 17 configured to limit or block blood from flowing therethrough. Occluding section 15 is selectively and fixedly compressible between distal body end 13 and proximal body end 14 parallel to longitudinal axis 11, from being stretched in delivery length DLL (as shown in FIG. 2A, for example) wherein the flow obstructing portions 17 extend substantially parallel to longitudinal axis 11, to being compressed in deployed length DPL (as shown in FIG. 1B and FIG. 2C, for example) wherein the flow obstructing portions 17 extend transversally to longitudinal axis 11. As shown, occluding section 15 is configured, when in the deployed length DPL, such that radially inner portions 18 of the plurality of tubular folds 16 and/or of distal and proximal body ends 13 and 14 are fixedly pressed tight against each other parallel to longitudinal axis 11. Occluding section 15 is optionally formed of a braided or interwoven sleeve interbraided from at least one wire and configured to expand in diameter when compressed longitudinally. Other portions of occluder body 12, such as structural elements comprising proximal body end 14 and/or distal body end 13, may be formed of other materials such as of metal or hard polymers.

Occluder body 12 encloses a lumen 27 that extends along longitudinal axis 11 and across the flow obstruction portions 17 also when occluding section 15 is compressed in its final deployed length DPL configuration. Tension member 28 may be provided integrated in vascular occluder 10 or as a separate member, in a kit for example. Tension member 28 is configured to pass through lumen 27 and to be fixedly connected to at least one of the body ends 13 and 14 or of one the flow obstruction portions 17, such that the occluding section 15 is longitudinally compressible from the delivery length DLL to the deployed length DPL along the elongated tension member 28 which is optionally coinciding with longitudinal axis 11 when taut parallel thereto.

Tension member 28 may be configured as a tether engaging a length securing member configured to resist lengthwise changes from the deployed length of occluding section 15 after being compressed to deployed configuration DPL. As such, tension member 28 may be part of a locking mechanism 19 and provided at one end of the occluder body 12 and configured to engage and selectively connect to a mating portion or member provided at another end of the occluder body, when occluding section 15 is in the deployed length DPL. Tension member 28 may be configured as a plastically deformable element or an elastically deformable element, optionally in a form of a wire or coil. Alternatively, tension member 28 is a flexible or malleable wire configured to preserve constant length without extending, thinning and/or tearing under normal tension forces applicable during implant deployment and after implantation. Tension member 28 may be configured to plastically deform when occluder body 12 is compressed longitudinally from the delivery length DLL to the deployed length DPL and/or when the occluder body 12 is forced to change in length from the deployed length DPL. Alternatively, tension member 28 is optionally configured to elastically relax (optionally not to a fully relaxed state) when occluder body 12 is compressed longitudinally from the delivery length DLL to the deployed length DPL and/or to elastically resist a change in length of occluder body 12 from the deployed length DPL.

Each one of the tubular folds 16 includes a pair of adjacent ascending portion 20 and descending portion 21, each one extending between respective outward apex 22 projecting away from longitudinal axis 11 and inward crease 23 projecting towards longitudinal axis 11. Each ascending portion 20 and/or each descending portion 21 includes one of the flow obstructing portions 17 between respective apex 22 and crease 23. A fold angle 24 formed between longitudinal axis 11 and the ascending or descending portion in each pair 16 is smaller than about 10°, optionally smaller than about 5°, when occluding section 15 is in the delivery length DLL and greater than about 15°, optionally greater than about 45°, optionally greater than about 80°, when occluding section 15 is in the deployed length DPL.

Each one of tubular folds 16 includes an anchoring portion 25 adjacent to the respective outward apex 22 thereof. When occluder body 12 compresses, a plurality of anchoring portions 25 are forced to expand in diameter sufficiently for engaging with and/or pressing against a target wall portion of a blood vessel, laterally outwardly to longitudinal axis 11, for fixating flow obstructing portions 17 to the target wall portion. The vascular occluder 10 is configured such that a plurality of the flow obstructing portions 17 are distant with each other when occluding section 15 is in the delivery length DLL and are compressed against each other when occluding section 15 is in the deployed length DPL. The plurality of the flow obstructing portions 17 is configured to obstruct blood flow therethrough when occluding section 15 is in the deployed length DPL or to allow a smaller rate of blood flowing therethrough than when occluding section 15 is in the delivery length DLL.

In some embodiments, in each fold 16, the respective radially inner portion 18 is located closer to the respective inward crease 23 than to the respective outward apex 22. In some embodiments, when occluding section 15 is in the deployed length DPL, the radially inner portions 18 of the plurality of folds 16 are deformed into a tight, compacted or condensed form with no gap therebetween, while radially outer portions 26 (peripheral or outward portions of folds 16 spaced radially outwardly from the radially inner portions 18) around it may be left looser and subjectable to conform to a shape imposed by walls of blood vessel BV. The radially outer portions 26 of folds 16 are also allowed to shift relatively to each other and/or to be arranged with gaps therebetween. Therefore, occluding section 15 in the deployed length DPL is thinnest adjacent to the radially inner portions 18 and optionally increasing gradually in thickness radially outwardly to radially inner portions 18.

As described above, the elongated occluder body 12 deliverable via the lumen of a catheter when occluding section 15 is stretched to the delivery length DLL and configured in a cylindrical-like form having a delivery diameter DD substantially constant along longitudinal axis 11. When occluding section 15 is in deployed length DPL, occluder body 12 is configured such that each one of tubular folds 16 is expandable to an anchoring diameter AD adjacently to the outward apex 22 thereof, measurable when in relaxed length RL. When expanded to anchoring diameter AD, that is substantially greater than inner diameter of the blood vessel at the implantation site, occluding section 15 is configured to apply an anchoring force laterally outwardly to longitudinal axis 11 for fixation to the target wall portion, being sufficient for facilitating engaging and pressing against a target wall portion of blood vessel BV. The anchoring force is optionally equal to or greater than 400 gr. Delivery diameter DD is optionally equal to or smaller than about 1.5 mm, optionally particularly equal to or smaller than about 1 mm, optionally particularly equal to or smaller than about 0.5 mm. Anchoring diameter AD is optionally equal to or greater than about 3 mm, optionally particularly greater equal to or greater than about 5 mm, optionally particularly equal to or greater than about 7 mm.

As will be described in more detail with respect to FIGS. 2 to 4, methods for occluding blood vessel BV can begin with inserting vascular occluder 10 into blood vessel BV proximately to a target wall portion TW thereof using a catheter 30. Catheter 30 may be designated for angiography and/or embolization of peripheral blood vessels, optionally having an inner lumen sized between about 0.45 mm and about 0.7 mm in diameter, and between about 100 cm and 150 cm in length, for example. When housed in catheter 30, occluding section 15 is maintained stretched in delivery length DLL. Occluding section 15 can be completely ejected from catheter 30 into blood vessel BV, optionally using a manually operable pusher 31, optionally releasably connected to occluder body 12, thereby optionally regaining a less stressed length (equal to or smaller than its relaxed length RL, for example). Occluding section 15 can then be initially compressed longitudinally, such that the plurality of tubular folds 16 with flow obstruction portions 17 thereof approximate each other, until being optionally substantially parallel with each other.

Following the initial compression, the operator (e.g., physician) can apply a further (e.g., final) compression (e.g., tightening) by which occluding section 15 is compressed to the fixed deployed length DPL. The operator can apply pusher 31 or distal end 35 of catheter 30, which are sized and configured to engage only radially inner portions 18, for pressing radially inner portions 18 tight against each other, parallelly to longitudinal axis 11, such that radially inner portions 18 are deformed into a tight, compacted or condensed form, optionally to a full extent with no gap therebetween. By pressing tight only radially inner portions 18, the radially outer portions 26 of the plurality of folds 16 are allowed to shift relatively to each other, and/or nest with each other, and may be subjected to conform to a radially compressed shape upon axial compression in response to external forces reacting thereon such as from the target wall portion TW.

As part of compressing occluder body 12 or upon tightening together radially inner portions 18, the flow obstructing portions 17 are subjected to a radial force being sufficient to fixate vascular occluder 10 to the target wall portion TW with by engaging directly with outward apexes 22 of tubular folds 16. The vascular occluder insertion may include positioning distal body end 13 or one or more (e.g., distal-most) of flow obstructing portions 17 adjacent to the target wall portion TW and the fixating includes pushing distal body end 14 and/or a proximal-most one of the flow obstructing portions 17 towards the distal body end 13 or the distal-most flow obstructing portion.

Referring back to FIGS. 2A-2C, FIG. 2A shows a first exemplary scenario in which catheter 30 is advanced distally in blood vessel BV until reaching close to target wall portion TW with a distal end 35 of catheter 30. Vascular occluder 10 may be readily provided in catheter 30 or advanced distally therein after catheter 30 is in blood vessel BV and/or distal end 35 is close to target wall portion TW. When residing in catheter 30, occluding section 15 is stretched in delivery length DLL configuration for allowing unhindered insertion into and passing through catheter 30 lumen. Elongated tension member 28 is fixated with distal end thereof to distal body end 13 of occluder body 12, with proximal end thereof is connected to a portion of catheter 30 or to another element in catheter 30, or is provided free and optionally extending out of patient's body. Pusher 31 is located in catheter 30 proximally to vascular occluder 10 and is configured to slide over tension member 28 and optionally to coincide substantially with longitudinal axis 11.

FIG. 2B shows a second exemplary scenario, after occluding section 15 has been completely ejected from catheter 30 within blood vessel BV, such that distal body end 13 of occluder body 12 is positioned adjacent to target wall portion TW. In some embodiments, this can be accomplished, such as following the first exemplary scenario in FIG. 2A, by holding pusher 31 in place while pulling proximally catheter 30, or by holding catheter 30 in place while advancing pusher 31 forward, or any combination thereof, until catheter 30 is withdrawn relatively to occluding section 15 as shown. In this scenario, occluding section 15 may be in relaxed length RL configuration, as shown, is partially radially compressed by target wall portion TW, and/or is partially compressed between pusher 31 and distal body end 13 (which may be held in place or pulled proximally with tension member 28) to a length between relaxed length RL and deployed length DPL.

FIG. 2C shows a third exemplary scenario after occluding section 15 is compressed into deployed length DPL configuration. As shown and as previously described, compression is made to a greater extent closer to longitudinal axis 11 at radially inner portions 18 of folds 16, making occluding section 15 substantially thinner in proximity to longitudinal axis 11 relative to radially outer portions 26 of folds 16. This configuration can be accomplished for example by pushing pusher 31 against radially inner portions 18 while holding distal body portion 13 of occluder body 12 in place (adjacent to target wall portion TW) using tension member 28 connected thereto. Occluder body 12 is configured to maintain occluding section 15 in deployed length DPL even if pusher 31 is withdrawn, optionally by use of tension member 28 shown in FIG. 1C. In some embodiments, distal portion or entire length of tension member 28 is configured as a tether (optionally by engaging with length securing member), and it is applied to resist or prevent extension of occluding section 15 from deployed length DPL. The operator may loosen occluding section 15 and redeploy vascular occluder 10 as needed, for example for repositioning. Once correctly implanted and anchored adjacent to target wall portion TW in blood vessel BV, catheter 30 and pusher 31 can be withdrawn, and tension member 28 can be also be withdrawn, left implanted and connected to occluder body 12 as an integral part of vascular occluder 10, and it may be cut in length for leaving only a distal portion thereof implanted.

Figures 3A, 3B, 3C:
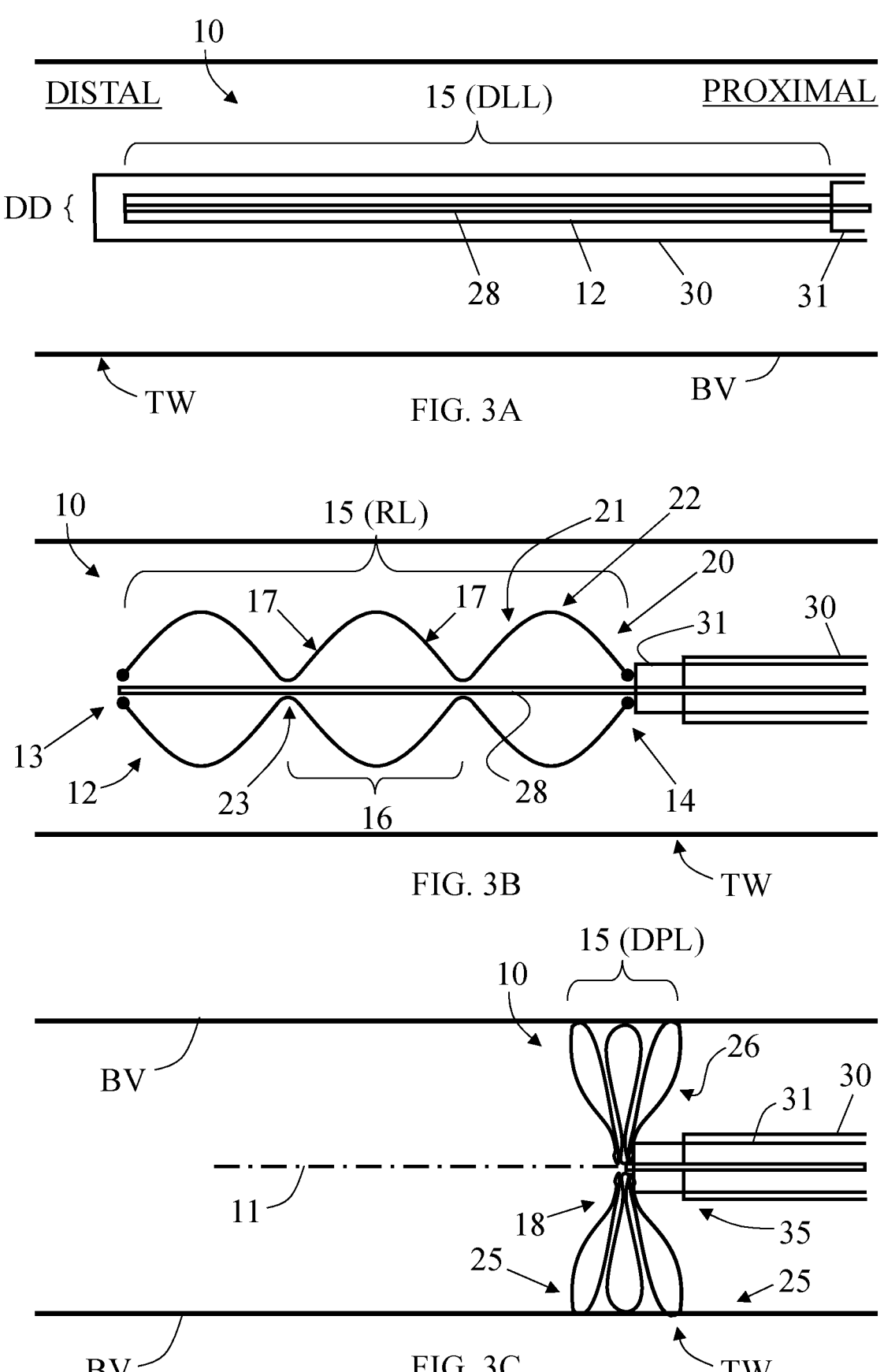
FIGS. 3A-3C schematically illustrate exemplary scenarios representing steps in a second exemplary procedure for implanting the exemplary vascular occluder of FIG. 1B, according to some embodiments.

FIGS. 3A-3C schematically illustrate exemplary scenarios representing steps in a second exemplary procedure for implanting vascular occluder 10 for occluding blood vessel BV. FIG. 3A shows a first exemplary scenario in which catheter 30 is advanced distally in blood vessel BV until reaching target wall portion TW with distal end 35 thereof. Vascular occluder 10 may be readily provided in a lumen of catheter 30 or advanced distally therein after catheter 30 is in blood vessel BV and/or distal end 35 sufficiently beyond target wall portion TW. When residing in catheter 30, occluding section 15 is stretched in delivery length DLL configuration for allowing unhindered insertion into and passing through catheter 30. Elongated tension member 28 is fixated with distal end thereof to distal body end 13 of occluder body 12, with proximal end thereof is connected to a portion of catheter 30 or to another element in catheter 30, or is provided free and optionally extending out of patient's body. Pusher 31 is located in catheter 30 proximally to vascular occluder 10, optionally releasably connected to proximal body end 14, and is configured for sliding over tension member 28 (optionally through a lumen thereof) when pulled or stretched to coincide substantially with longitudinal axis 11.

FIG. 3B shows a second exemplary scenario, after occluding section 15 has been completely ejected from catheter 30 within blood vessel BV, such that proximal body end 14 of occluder body 12 is positioned adjacent to target wall portion TW and distal body end 13 is positioned distally beyond target wall portion TW. In some embodiments, this can be accomplished, such as following the first exemplary scenario in FIG. 3A, by pushing pusher 31 distally until distal end thereof is close to target wall portion TW, while holding catheter 30 in place until occluding section 15 is completely ejected, as shown. In this scenario, occluding section 15 may be in relaxed length RL configuration, as shown, or is partially compressed between pusher 31 and distal body end 13, which may be held in place or pulled proximally with tension member 28, to a length between relaxed length RL and deployed length DPL.

FIG. 3C shows a third exemplary scenario after occluding section 15 is compressed into deployed length DPL configuration with distal body end 13 put in proximity to target wall tissue TW. As shown and as previously described, folds 16 compression is made to a greater extent closer to longitudinal axis 11 at radially inner portions 18 of folds 16, making occluding section 15 substantially thinner in proximity to longitudinal axis 11 relative to radially outer portions 26 of folds 16. This configuration can be accomplished by pulling tension member 28 proximally until radially inner portions 18 sufficiently pressed against pusher 31 while holding pusher 31 and/or catheter 30 in place, with pusher 31 distal end and proximal body end 14 being adjacent to target wall portion TW. Occluding section 15 is configured to maintain its deployed length DPL even if pusher 31 is withdrawn, optionally by use of tension member 28 shown in FIG. 1C as a tether, such as for locking occluder body in the deployed configuration. The operator may loosen and redeploy vascular occluder 10 as needed, for example for repositioning. Once correctly implanted and anchored adjacent to target wall portion TW in blood vessel BV, catheter 30 and pusher 31 can be withdrawn, and tension member 28 can also be withdrawn, left implanted and connected to occluder body 12 as an integral part of vascular occluder 10, and cut in length leaving distal portion thereof implanted.

Figures 4A, 4B, 4C:
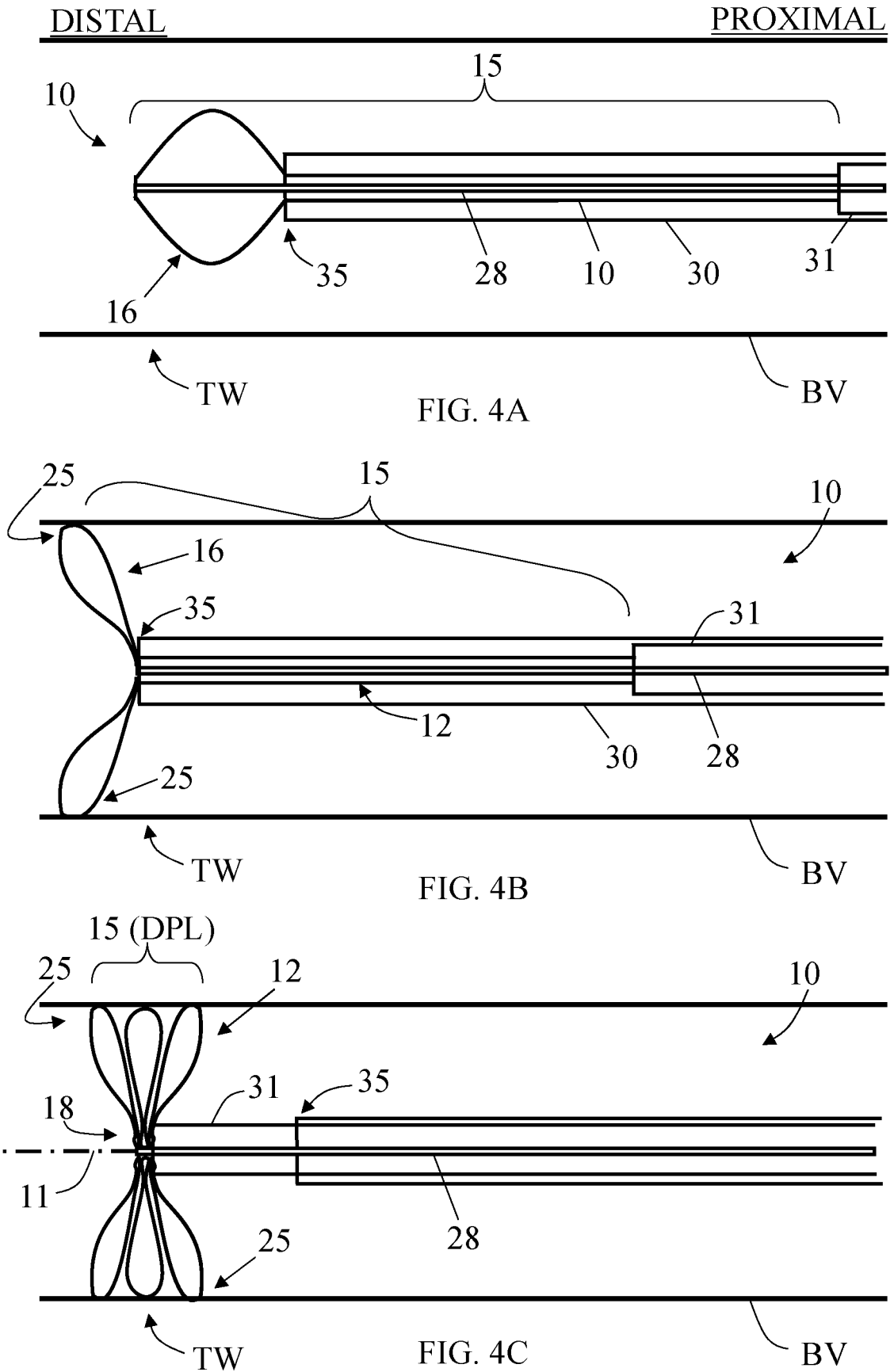
FIGS. 4A-4C schematically illustrate exemplary scenarios representing steps in a third exemplary procedure for implanting the exemplary vascular occluder of FIG. 1B, according to some embodiments.

FIGS. 4A-4C schematically illustrate exemplary scenarios representing steps in a third exemplary procedure for implanting vascular occluder 10 for occluding blood vessel BV. In this exemplary embodiment, the ejection of occluding section 15 from catheter 30 and then compression to deployed length DPL is not done at once but rather sequentially and/or gradually, one or more of folds 16, or portion thereof at a time, thereby allowing a more localized procedure with shorter vessel length required for the complete extension of occluding section 15 before compression. Catheter 30 with vascular occluder 10 can be advanced until reaching target wall portion TW with distal end 35 of catheter 30, similarly to as shown in FIG. 2A, for example. FIG. 4A shows a first exemplary scenario in which a distal-most one of folds 16 is ejected from catheter 30, while remainder of occluding section 15 is kept stretched within catheter 30. This can be accomplished for example by first withdrawing catheter 30 proximally to target wall portion TW to a distance similar to a relaxed length of a single fold 16 (in this example, about third of relaxed length RL as there are three tubular folds 16 for example), while holding pusher 31 in place, then releasing sufficient length of tension member 28 for allowing expansion of single fold 16 in blood vessel BV outside of catheter 30, and finally withdrawing pusher 31 while holding catheter 30 in place. Alternatively, folds 16 can be formed sequentially by pushing pusher 31 and holding catheter 30 and tension member 28 in place until sufficient length of occluding section 15 is ejected, then allowed to compress to a less elastically stressed form, per ejection of each fold 16.

FIG. 4B shows a second exemplary scenario in which distal-most fold 16 is separately compressed and held fully compressed with pusher 31 and/or distal end 35. This can be accomplished for example by pulling distal-most fold 16 against catheter distal end 35, or by pushing pusher 31 and/or catheter distal end 35 against radially inner portion 18 of the distal-most fold 16 while holding in place or pulling tension member 28. The first exemplary scenario followed by the second exemplary scenario can then be repeated, sequentially, per each additional fold or part thereof until all of occluding section 15 protrudes distally from catheter 30 and fully compressed. Optionally, use of other or additional means, such as directional spikes on the outer surface of the occluder body 12, for example, can resist or prevent longitudinal extension of each fold after occluding section 15 is fully compressed.

FIG. 4C shows a third exemplary scenario after occluding section 15 is entirely compressed into deployed length DPL configuration. As shown and as previously described, compression is made to a greater extent closer to longitudinal axis 11 at radially inner portions 18 of folds 16, making occluding section 15 substantially thinner in proximity to longitudinal axis 11 relative to radially outer portions 26 of folds 16. This configuration can be accomplished by repeating the some or all steps described with respect to scenarios of FIGS. 4A and 4B, each time for ejecting and then compressing a single fold separately to other folds 16, until entire occluding section 15 is ejected and compressed. Occluding section 15 is configured to maintain its deployed length DPL even if pusher 31 is withdrawn, optionally by use of tension member 28 shown in FIG. 1C as a tether. The operator may loosen, withdraw and redeploy vascular occluder 10 as needed, for example for repositioning. Once correctly implanted and anchored adjacent to target wall portion TW in blood vessel BV, catheter 30 and pusher 31 can be withdrawn, and tension member 28 can also be withdrawn, left implanted as part of vascular occluder 10, or cut in length leaving distal portion thereof connected to and implanted with vascular occluder 10.

Vascular occluder 10, or exemplary configurations or variations thereof in structure, function and/or modality, can be applied in a variety of methods of treatment. In some embodiments, a method of occluding a passage in a body of a live subject can include: (a) inserting a vascular occluder into the passage, while maintaining the occluding section in the delivery configuration; (b) releasing the occluding section in the passage from the delivery configuration such that the occluding section is allowed to shorten and laterally expand, selectively or autonomously, into a less elastically stressed configuration; (c) compressing longitudinally the occluding section into the deployed configuration by increasing longitudinal elastic stress of the occluding section relative to the less elastically stressed configuration, thereby occluding the passage; and (d) locking the occluding section in the deployed configuration.

The method may further include advancing a catheter enclosing a catheter lumen through a blood vessel, such that a distal opening of the catheter lumen is positioned in the passage.

The method may further include pushing the vascular occluder with a pusher releasably connected to the occluder body until protruding at least partially the occluding section in the passage via the distal opening. Inserting the vascular occluder to the passage may include the pushing thereof with the pusher.

Releasing the occluding section in the passage from the delivery configuration may include reducing tension in the tension member. Compressing longitudinally the occluding section into the deployed configuration may include increasing tension in the tension member sufficiently to compress and lock the occluding section in the deployed configuration.

The method may further include disconnecting the pusher from the occluder body. Disconnecting the pusher may include releasing the pusher from being rigidly connected to the occluder body, and/or cutting the tension member optionally distally to the pusher.

Releasing or compressing longitudinally the occluding section may include bending at least one of the bellows sections towards the longitudinal axis, and the compressing longitudinally or locking includes generating continuous internal stresses configured to hold the at least one of the bellows sections bent towards the longitudinal axis, thereby locking the occluding section in the deployed configuration.

Compressing longitudinally the occluding section may include applying tension to the tension member, and the locking the occluding section may include fastening a portion of the tension member to the proximal body end of the occluding section when in the deployed configuration for preventing or resisting elongation from the deployed length.

Locking the occluding section may include or be followed by disjoining or cutting the tension member to a predetermined length by applying tension thereto above a chosen tension force.

The passage may be a blood vessel and the occluding may affect (cause) immediate or gradual cessation of blood flow through the occluding section in the blood vessel. The passage may alternatively include an opening in an organ wall separating between distinct organ lumens. The organ wall may be a blood vessel wall and the method may then be configured to treat vessel wall aneurism or a patent ductus arteriosus; alternatively, the organ wall may be a septal wall and the method may then be configured to treat a septal defect such as an atrial septal defect. In some such embodiments, inserting the vascular occluder into or through the passage may include passing the occluder body through the opening. Releasing the occluding section may include first releasing a distal portion of the occluding section distally to the organ wall and later releasing a proximal portion of the occluding section proximally to the organ wall, such that compressing the occluding section aims to occlude the opening.

FIGS. 5A-5F schematically illustrate exemplary scenarios representing steps in an exemplary procedure for treating an aneurism ANM in a blood vessel, optionally target blood vessel BV, using an exemplary variation 10' of vascular occluder 10. Aneurysms such as aneurism ANM are a type of vascular abnormality, manifesting a local outwards bulging from the wall of a blood vessel, and may be formed as a result of blood vessel's weak portions yielding under pressure. The space formed with aneurism ANM is opened to lumen of blood vessel BV via an opening formed through a neck portion ANP of aneurism ANM adjoining with blood vessel BV. Vascular occluder 10' may be similar or identical to vascular occluder 10, and in some embodiments may differ at least by the number of tubular folds 16 it includes and/or shape and/or dimension of one or more of folds 16. In some embodiments, vascular occluder 10' is configured for treating aneurisms in order to reduce risk of aneurism and/or blood vessel raptures or hemorrhages; to diminish or prevent aneurism pressing against adjacent organs or vessels; and/or to prevent clot formation in or adjacent to the aneurism.

Figure 5A:
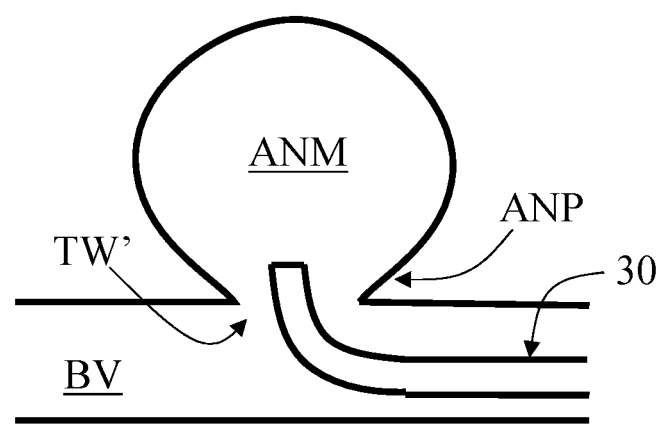
FIGS. 5A-5F schematically illustrate exemplary scenarios representing steps in an exemplary procedure for treating an aneurism in a target blood vessel using an exemplary variation of the exemplary vascular occluder of FIG. 1B, according to some embodiments.
Figure 5B:
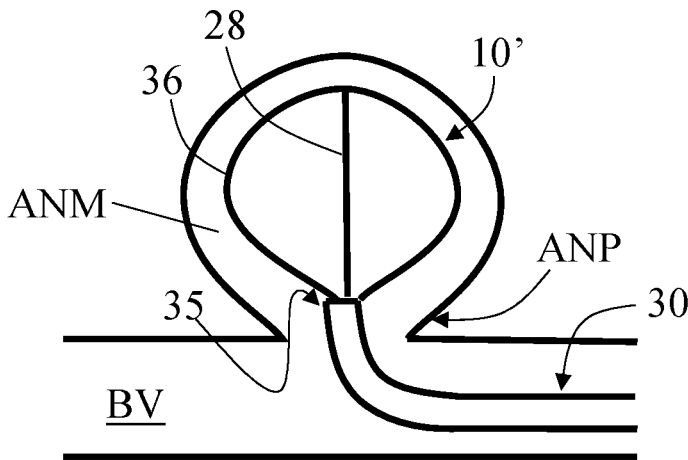

As shown in FIG. 5A, catheter 30 is advanced in blood vessel BV towards aneurism ANM and distal end 35 thereof may be inserted into the space formed by aneurism ANM through the opening of neck portion ANP of aneurism ANM. Catheter distal end 35 may be curved, bent, and/or flexed in the direction of the aneurism ANM in order to allow or ease insertion into aneurism ANM. Vascular occluder 10' is inserted into blood vessel BV proximately to a new target wall portion TW' of the blood vessel BV adjacent to aneurism ANM, and then ejected from catheter 30 in a sequential scheme. As shown in FIG. 5B, a distal-most fold 36 of tubular folds 16 is first ejected into the space formed by aneurism ANM, distally to neck portion ANP, and is allowed or forced to expand in aneurism ANM at least it has dimension greater than the opening of neck portion ANP so that it cannot migrate therethrough into blood vessel BV.

Figure 5C:
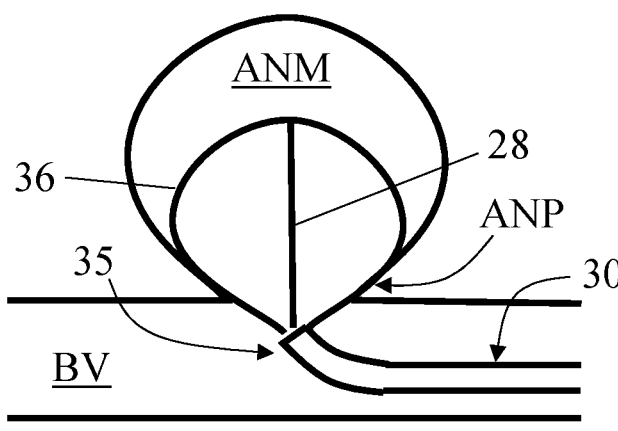
Figure 5D:
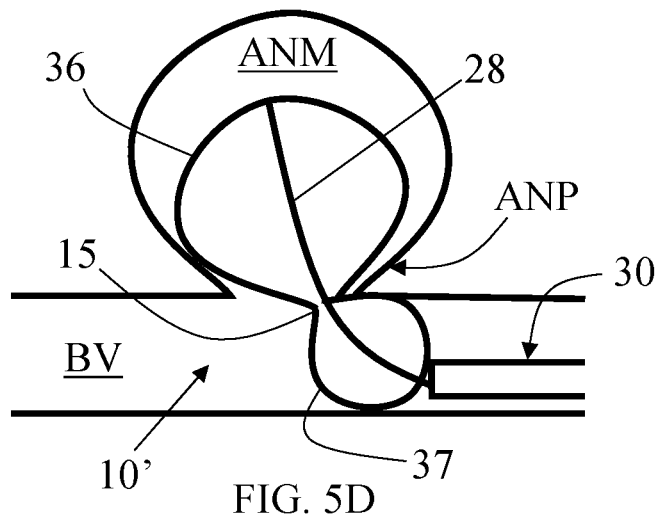
Figure 5E:
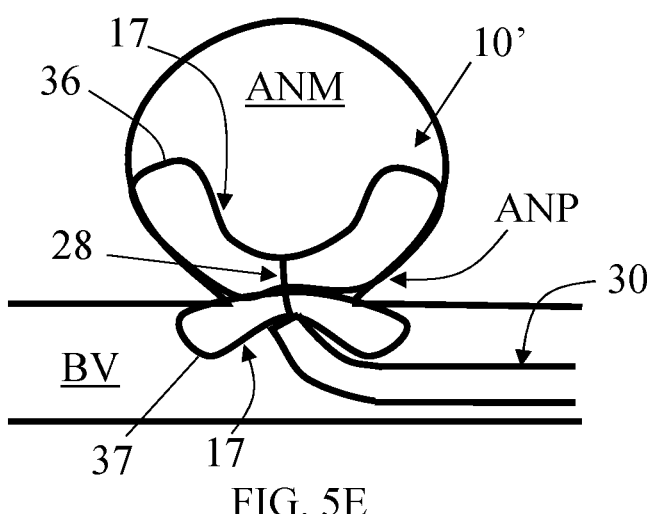

The expanded distal-most fold 36 is then pulled proximally optionally together with partially withdrawing catheter 30 until it is pressed against neck portion ANP (FIG. 5C). A proximal-most fold 37 of tubular folds 16 can then be ejected from catheter 30 in blood vessel BV proximally to neck portion ANP, as shown in FIG. 5D. As shown in FIG.

5E, occluding section 15 can be gradually compressed so that the plurality of tubular folds 16 are compressed longitudinally such that the flow obstruction portions 17 thereof are adjacent such and parallel to each other and to neck portion ANP. Upon longitudinal compression, occluding portion 15 is configured to cause blocking of blood from flowing, or reducing rate of blood flow, through the flow obstructing portions 17.

Figure 5F:
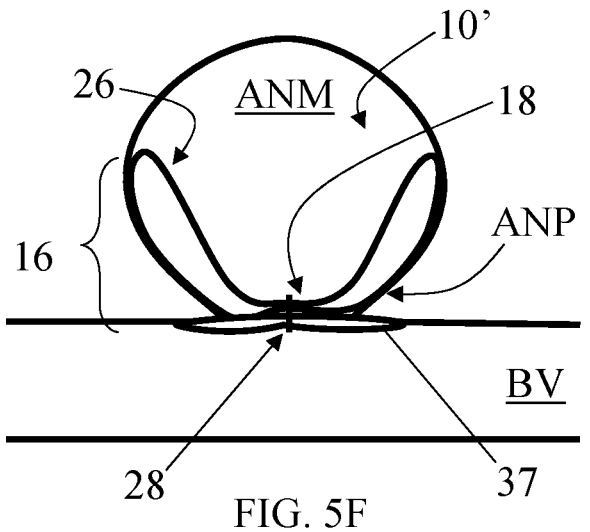

As shown in FIG. 5F, radially inner portions 18 of the plurality of tubular folds 16 are then pressed tight (tightened) against each other, and fixated in this state, while radially outer portions 26 of the plurality of tubular folds 16 are allowed to shift relative to each other and/or to arrange with gaps therebetween. Tightening of folds 16 locks vascular occluder 10 to neck portion ANP by leaving distalmost fold 36 continuously (e.g., permanently) pressed against the proximal-most fold 37 across neck portion ANP. Tension member 28 can then be disconnected or released from holding by or via catheter 30, and catheter 30 can be withdrawn completely from blood vessel BV, as shown. In some embodiments, compressing longitudinally and/or the pressing tight of (tightening) tubular folds 16 includes applying tension to distal end of occluding section 15 via tension member 28, while pushing distally proximal end of occluding section 15, directly to and/or across radially inner portions 18. In some embodiments, compressing and/or tightening tubular folds 16 across neck portion ANP deforms proximal-most fold 37 into a narrow or flat disk-like shape greater in diameter than the opening in neck portion ANP. The disk-like shape may be curved with radially outer portions 26 thereof towards distal-most fold 36 for decreasing interference to blood flow in blood vessel BV. In some embodiments, compressing and/or tightening tubular folds 16 across neck portion ANP deforms distal-most fold 36 into a toroid-like shape having flattened radially inner portion 18 and partially expanded radially outer portion 26 being rounded adjacent apex thereof so as to minimize damage to aneurism ANM wall portion in contact.

FIGS. 6A-6F schematically illustrate exemplary scenarios representing steps in an exemplary procedure for occluding an opening OP in an organ wall ORW with vascular occluder 10' being an exemplary configuration of vascular occluder 10. Organ wall ORW separates between distinct organ lumens or cavities—first organ lumen OL1 and second organ lumen OL2—and a passage, configured as opening OP, formed across the two organ lumens may be a result of an artificial or a naturally occurring defect, required to be occluded in some situations. A first example includes heart septal defects, most common of which is 'atrial septal defect' (ASD), a congenital heart defect in which blood flows between the atria of the heart. A second example includes defects in blood vessel walls, including for example situations of arteriovenous shunts or malformations, where arteries and veins form direct connections, or 'patent ductus arteriosus' (PDA) in which the ductus arteriosus fails to close after birth allowing a portion of oxygenated blood from the left heart to flow back to the lungs via the aorta to the pulmonary artery.

Figure 6A:
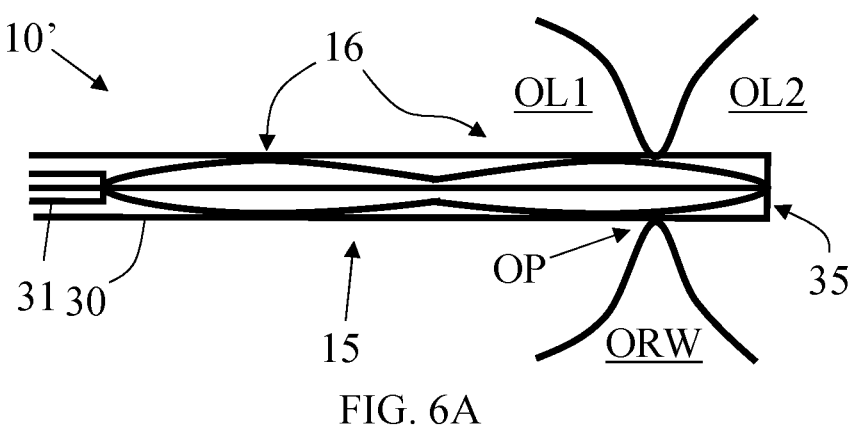
FIGS. 6A-6F schematically illustrate exemplary scenarios representing steps in an exemplary procedure for occluding an opening in an organ wall with the exemplary vascular occluder of FIG. 1B, according to some embodiments.
Figure 6B:
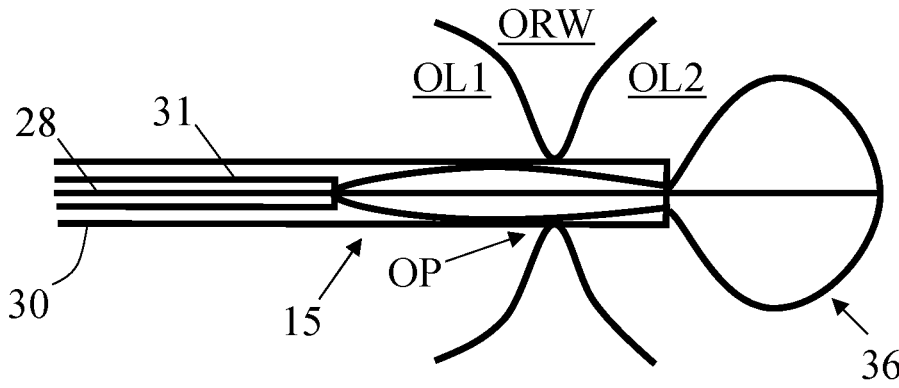

As shown in FIG. 6A, catheter 30 is advanced in first organ lumen OL1 and pushed through opening OP, such that distal end 35 thereof is inserted into second organ lumen OL2. By causing relative motion between catheter 30 and pusher 31 (e.g., catheter 30 is held in-place or withdrawn and/or pusher 31 is pushed distally or held in-pace, respectively), a distal portion of occluding section 15, such as distal-most fold 36 of tubular folds 16 in its entirety, is inserted into second organ lumen OL2, and then ejected from catheter 30 in a sequential scheme. As shown in FIG. 6B, distal-most fold 36 is first ejected into second organ lumen OL2, distally to opening OP, and is allowed or forced to expand in second organ lumen OL2 at least to a dimension greater than opening OP so that it cannot migrate therethrough back into first organ lumen OL1.

Figure 6C:
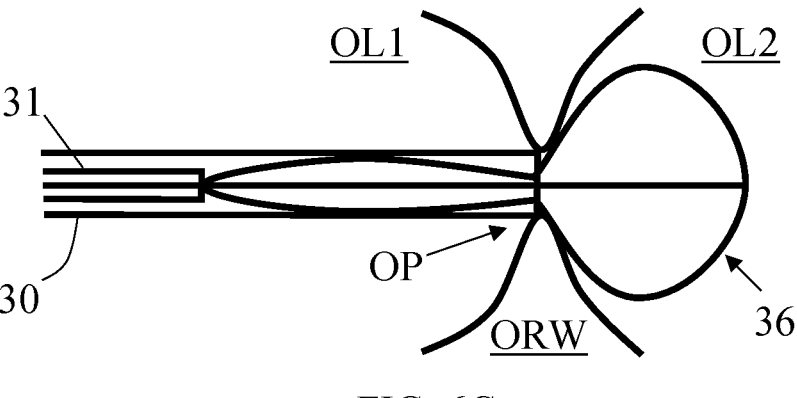
Figure 6D:
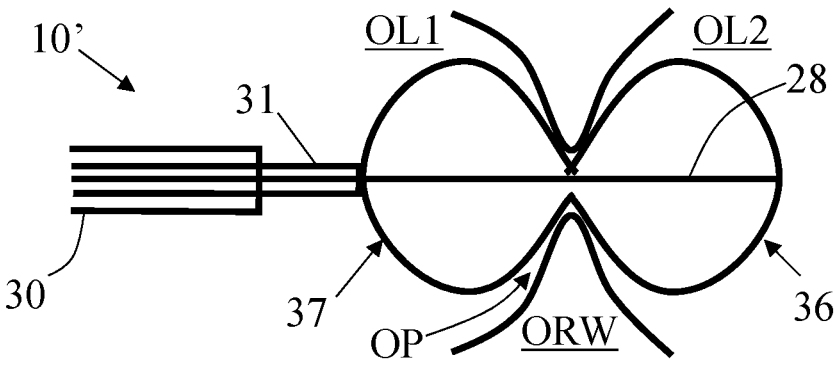

The expanded distal-most fold 36 is then pulled proximally optionally together with partially withdrawing catheter 30 until it is pressed against organ wall ORW (FIG. 6C). A proximal portion of occluding section 15, such as proximal-most fold 37 of tubular folds 16, can then be ejected from catheter 30 in first organ lumen OL1 proximally to opening OP, as shown in FIG. 6D. Occluding section 15 can be gradually compressed so that the plurality of tubular folds 16 are compressed longitudinally such that the flow obstruction portions 17 thereof are adjacent and/or substantially parallel to each other and to organ wall ORW.

Figure 6E:
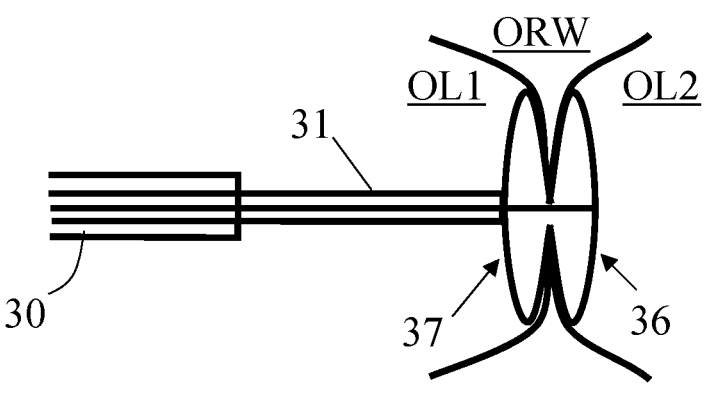
Figure 6F:
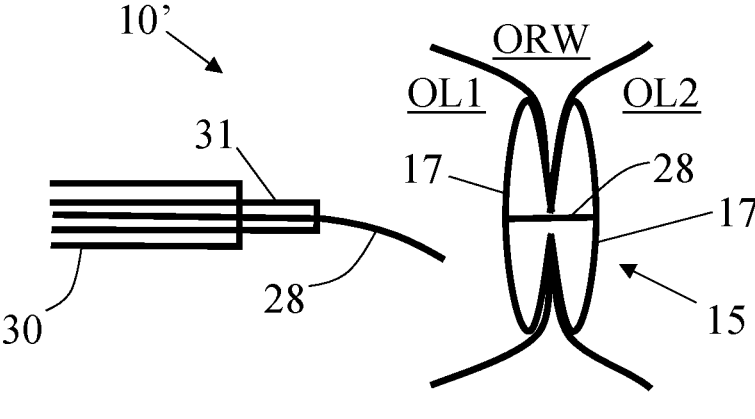

As shown in FIG. 6E, radially inner portions 18 of the plurality of tubular folds 16 are then pressed tight (tightened) against each other and fixated in this state. Upon longitudinal compression, occluding portion 15 is configured to cause blocking of blood from flowing, or reducing rate of blood flow, through the flow obstructing portions 17. Tightening of folds 16 also locks vascular occluder 10' to organ wall ORW by leaving distal-most fold 36 continuously (e.g., permanently) pressed against the proximal-most fold 37 from both sides thereof. Tension member 28 can then be disconnected or cut from holding by or via catheter 30, and catheter 30 can be withdrawn completely from blood vessel BV, as shown in FIG. 6F.

Figures 7A, 7B, 8A, 8B:
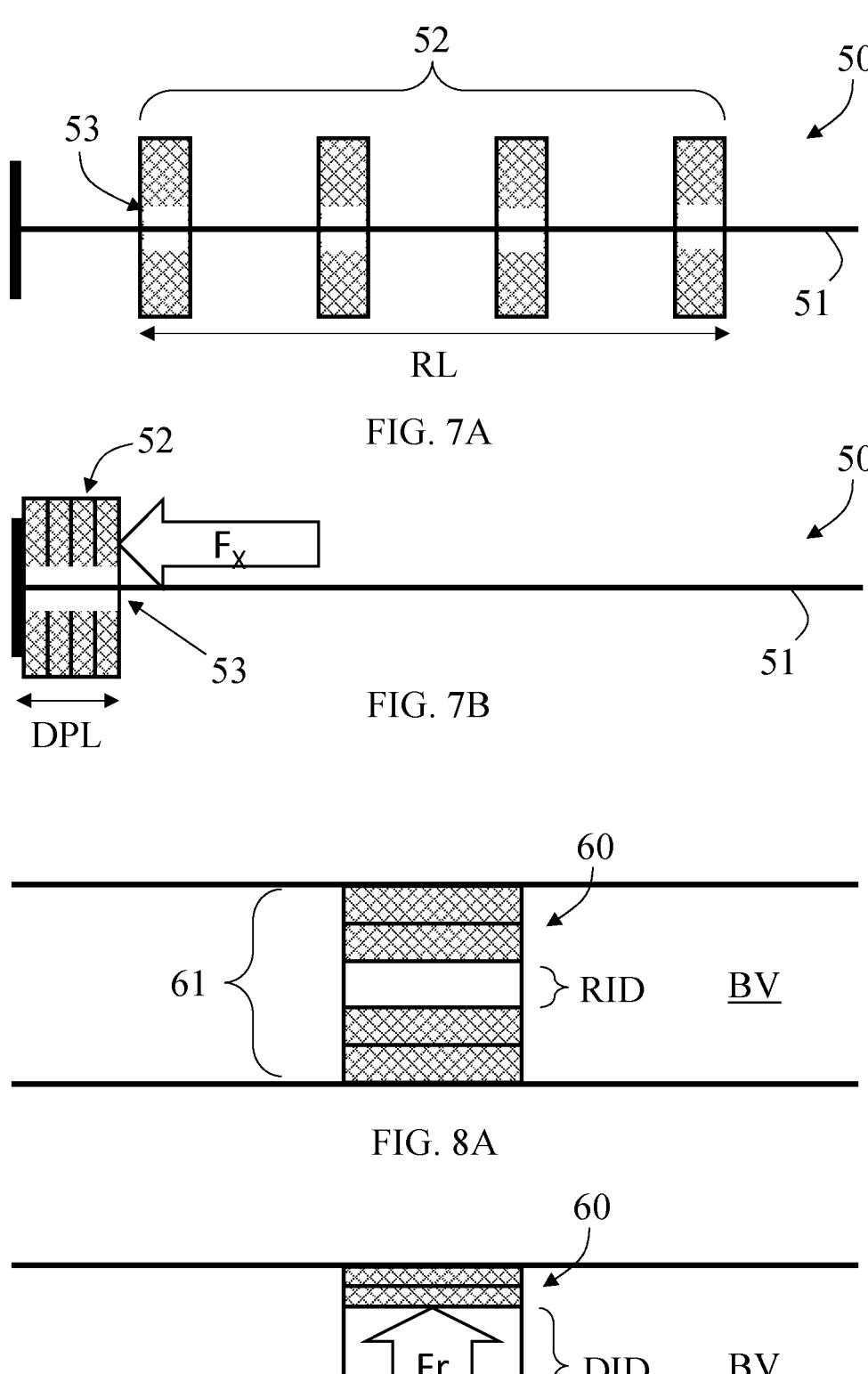
FIGS. 7A-7B schematically illustrate respectively an exemplary vascular occluder with flow obstructing portions before and after axial compression thereof, according to some embodiments.
FIGS. 8A-8B schematically illustrate respectively an exemplary vascular occluder with flow obstructing portions before and after radial compression thereof, according to some embodiments.
Figures 9A, 9B, 10:
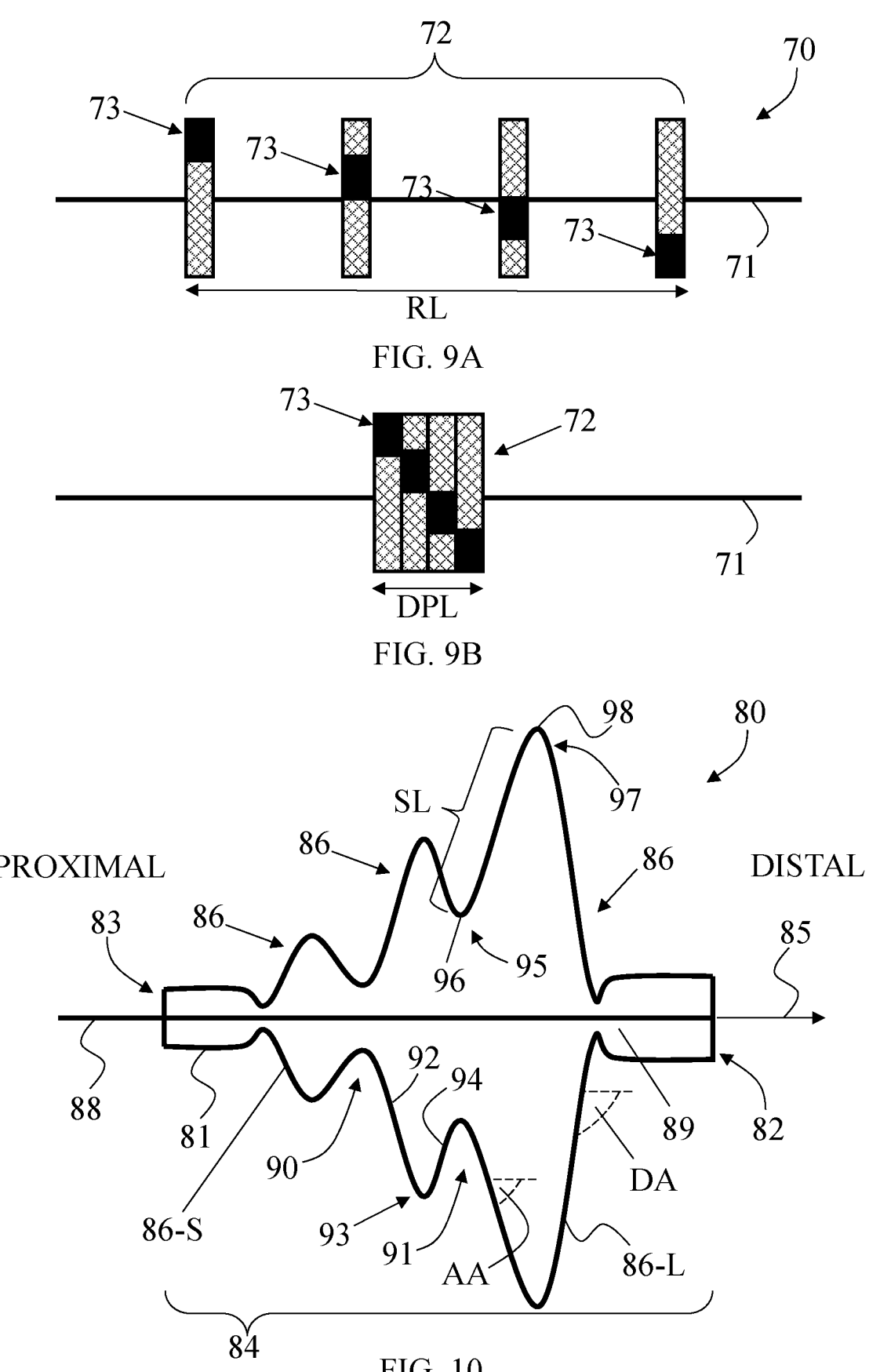
FIGS. 9A-9B schematically illustrate respectively an exemplary vascular occluder with flow obstructing portions varying in radial location of less permeable region thereof, before and after axial compression thereof, according to some embodiments.
FIG. 10 schematically illustrates an exemplary vascular occluder comprising a plurality of bellows sections varying in diameter, according to some embodiments.

The following FIGS. 7, 8 and 9 depicts three conceptual features, one or more of which may be incorporated in exemplary embodiments described herein. The first conceptual feature illustrated in FIGS. 7A-7B is aimed for selectively affecting reduced permeability of an exemplary vascular occluder 50 when portions thereof are compressed axially against each other (e.g., parallel to longitudinal axis of vascular occluder 50). The second conceptual feature illustrated in FIGS. 8A-8B is aimed for selectively affecting increase in radial strength and/or particularly in resistance to radial inward compression of an exemplary vascular occluder 60 when portions thereof are compressed radially outwardly against each other (e.g., radially to longitudinal axis of vascular occluder 60). The third conceptual feature illustrated in FIGS. 9A-9B is aimed for selectively affecting substantial impermeability of an exemplary vascular occluder 70 when portions thereof are approximated and/or placed in contact each other. Vascular occluder 80 shown in FIGS. 10-11 is provided as an exemplary device designed for encompassing all three conceptual features for use in occluding bodily lumens such as blood vessels.

FIGS. 7A-7B schematically illustrate vascular occluder 50 which may be an exemplary implementation or variation of vascular access port 10 and/or 10', and/or it may include some or all embodiments and features of vascular access port 10 and/or 10', and/or be identical or similar in function, structure and/or modality to vascular access port 10 and/or 10'. vascular occluder 50 comprising of a tension member 51 and a plurality of flow obstruction portions 52 provided sequentially along a portion of tension member 51 and extending at least partially transversely thereto. Each one of the flow obstruction portions 52 is partially permeable to blood flowing therethrough and is sized and configured to cover most or all cross section of the bodily lumen portion it is prescribed to treat. Optionally, each one of the flow obstruction portions 52 includes a mesh pattern and/or a braided or interwoven structure with mesh openings sized to allow blood flow therethrough, yet optionally to cause some degree of obstruction thereto. Tension member 51 passes through a respective lumen 53 of each one of the flow obstruction portions 52 such that one or more of the plurality of flow obstruction portions 52 is movable axially over the tension member 51 relative to remainder of the flow obstruction portions.

Flow obstruction portions 52 are selectively compressible against each other axially (e.g., in a direction parallel to the tension member and/or the route defined by the bodily lumen treated) by a longitudinal (axial) compression force $F_X$, from a more elastically relaxed length RL (FIG. 7A) to a fixable deployed length DPL (FIG. 7B), such that radially inner portions thereof are pressed tight against each other. Deployed length DPL can be fixated or locked by self-locking mechanism or structure and/or by using locking-specific means.

Vascular occluder 50 is configured less permeable to blood flowing therethrough in the bodily lumen when the plurality of flow obstruction portions 52 is in the deployed length DPL than when the plurality of flow obstruction portions 52 is in the more elastically relaxed length RL. In some embodiments, reduction in permeability results from the particular fluid permeable structure of each one of the obstruction portions 52 that derives a specific (e.g., predetermined fluid flow pattern or regime therethrough, while approximating and/or contacting the plurality of flow obstruction portions 52 axially into a smaller volume further affects the flow regime by increasing the density of obstacles to axial flow therethrough. In similar or other embodiments, each one of the flow obstruction portions 52 is forced to compress to a thinner form while causing structural deformation that reduces its own permeability to fluid flowing therethrough.

The plurality of flow obstruction portions 52 may be provided as separate (distinct) members as shown, or they may be portions of a single structure, as will demonstrated in a particular exemplary embodiment with respect to vascular occluder 80. In some embodiments, vascular occluder 50 includes an elongated occluder body comprising an occluding section wherein the plurality of flow obstruction portions 52 forms the occluding section or part thereof.

FIGS. 8A-8B schematically illustrate vascular occluder which may be an exemplary implementation or variation of vascular access port 10, 10' and/or 50, and/or it may include some or all embodiments and features of vascular access port 10, 10' and/or 50, and/or be identical or similar in function, structure and/or modality to one or more of vascular access ports 10, 10', and 50. Vascular occluder 60 comprising a plurality of anchoring portions 61 provided concentrically one over the other at a target portion of a blood vessel BV. In some embodiments, the plurality of anchoring portions 61 form together a structure configured to obstruct a normal flow of blood therethrough in the blood vessel BV, and each one of the anchoring portions 61 is optionally partially permeable to blood flowing therethrough. Optionally, each one of anchoring portions 61 includes a mesh pattern and/or a braided or interwoven structure with mesh openings sized to allow blood flow therethrough, yet optionally to cause some degree of obstruction thereto.

Vascular occluder 60 is configured to self-anchor to wall of blood vessel BV by expanding to a more elastically relaxed configuration such that it becomes in contact with periphery (radially outer portion) thereof with the blood vessel wall and optionally forces the blood vessel wall to expand locally. In some embodiments, the resistance to radial inward compression in this more elastically relaxed configuration is insufficient for continuous or permanent anchoring and for preventing migration, for example when local diameter of the blood vessel wall portion is in constant change such as due to wall muscle activity and changes between systolic and diastolic pressures.

In order to overcome such potential issues, vascular occluder 60 is configured to selectively increase its resistance to radial inward compression by the blood vessel wall. As such, anchoring portions 61 are selectively compressible radially outwardly against each other and against wall of blood vessel BV (e.g., in a direction orthogonal to the route defined by the bodily lumen treated, in this case blood vessel BV), by selectively applying a radial force or pressure Fr thereto, from a more elastically relaxed inner diameter RID (FIG. 8A) to a fixable deployed inner diameter DID (FIG. 8B), such that radially inner portions 62 thereof are pressed tight against each other. Deployed inner diameter DID can be fixated or locked by self-locking mechanism or structure and/or by using locking-specific means. When locked in the deployed inner diameter DID, the plurality of anchoring portions 61 provides substantially greater resistance to radial inward compression than when the plurality of anchoring portions 61 is in the more elastically relaxed inner diameter RIL.

In some embodiments, increase in radial strength and/or resistance to radial compression results from a continuous application of outward force (or pressure) that forces inner anchoring portions against the outer anchoring portion, when vascular occluder 60 is locked in the deployed configuration. In similar or other embodiments, each one of the anchoring portions 61 is forced to compress elastically to a thinner form while causing structural deformation that increases the overall springback of the plurality of anchoring portions 61 such that greater forces are then required to compress the vascular occluder to a smaller outer diameter.

The plurality of anchoring portions 61 may be provided as separate (distinct) members, or they may be portions of a single structure, as will demonstrated in a particular exemplary embodiment with respect to vascular occluder 80. In some embodiments, vascular occluder 60 includes an elongated occluder body comprising an occluding section wherein the plurality of anchoring portions 52 forms the occluding section or part thereof.

FIGS. 9A-9B schematically illustrate vascular occluder 70 which may be an exemplary implementation or variation of vascular access port 10, 10', 50 and/or 60, and/or it may include some or all embodiments and features of vascular access port 10, 10', 50 and/or 60, and/or be identical or similar in function, structure and/or modality to one or more of vascular access ports 10, 10', 50, and 60. Vascular occluder 70 comprising of a tension member 71 and a plurality of flow obstruction portions 72 provided sequentially along a portion of tension member 71 and extending at least partially transversely thereto. One or more of the plurality of flow obstruction portions 72 is movable axially over the tension member 71 relative to remainder of the flow obstruction portions. Each one of the flow obstruction portions 72 is partially permeable to blood flowing therethrough and is sized and configured to cover most or all cross section of the bodily lumen portion it is prescribed to treat. Furthermore, each one of the flow obstruction portions 72 includes at least one region 73 that is less permeable to blood flow therethrough than remainder of the particular flow obstruction portion, such that blood will normally tend to flow around region 73 through remainder of the flow obstruction portion than through region 73. In some embodiments, region 73 is impermeable to blood flow.

Optionally, each one of the flow obstruction portions 72 includes a mesh pattern and/or a braided or interwoven structure with mesh openings sized to allow blood flow therethrough, yet optionally to cause some degree of obstruction thereto. In some such embodiments, less permeable region 73 will have denser pattern and/or thicker yarns for example or will be made impermeable using a localized covering or impregnated material over the mesh pattern.

As shown, flow obstructing portions 72 vary in radial location of their respective less permeable region 73, meaning that in some or all flow obstructing portions 72 the respective region 73 will be located in a different radial distance and/or radial direction away from centerline and/or longitudinal axis of vascular occluder 70. This means that a stream pattern of blood caused by passing through one of the flow obstructing portions 72 will change when approaching and/or passing through the next flow obstructing portion due to the tendency to avoid or flow around region 73 of a different radial location.

As such, vascular occluder 70 is configured less permeable to blood flowing therethrough in the bodily lumen when the plurality of flow obstruction portions 72 is in the deployed length DPL (as shown in FIG. 9A) than when the plurality of flow obstruction portions 72 is in the more elastically relaxed length RL (as shown in FIG. 9B). This may happen for example since that when the flow obstructing portions are distant from each other the blood flow can maneuver and adapt its flow pattern in between each consecutive flow obstruction portions 72, while when the flow obstruction portions are in contact with each other in a compressed form the blood has fewer cross sectional areas not covered with any of the less permeable or impermeable regions 73 forcing them either to flow through or be blocked by regions 73.

Additionally or alternatively, regions 73 changes in permeability to blood flow when and/or as a result of the longitudinal (axial) compression of flow obstruction portions 72, collectively forming an obstructing section of vascular occluder 70, into a deployed configuration resulting in deployed length DPL. Change in permeability can be affected for example when structural openings or pores in regions 73 reduces in size and/or when regions 73 become denser, for example due to compression thereof. Such change in permeability may cause reduced flow rate of blood passing through regions 73 or complete blockage thereof, comparing to the flow pattern of the structural and/or functional state of flow obstruction portions 72 in the more elastically relaxed length RL. The plurality of flow obstruction portions 72 may be provided as separate (distinct) members as shown, or they may be portions of a single structure, as will demonstrated in a particular exemplary embodiment with respect to vascular occluder 80. In some embodiments, vascular occluder 70 includes an elongated occluder body comprising an occluding section wherein the plurality of flow obstruction portions 72 forms the occluding section or part thereof.

FIG. 10 schematically illustrates exemplary vascular occluder 80 comprising a plurality of bellows sections varying in diameter, and FIGS. 11A-11D schematically illustrate exemplary scenarios representing steps in an exemplary procedure for implanting vascular occluder 80 in a bodily lumen such as blood vessel BV. Vascular occluder 80 includes an elongated occluder body 81 comprising a distal body end 82, a proximal body end 83 and an occluding section 84 extending along a longitudinal axis 85 between distal body end 82 and proximal body end 83. Vascular occluder 80 may be an exemplary implementation or variation of vascular access port 10, 10', 50, 60 and/or 70, and/or it may include some or all embodiments and features of vascular access port 10, 10', 50, 60 and/or 70, and/or be identical or similar in function, structure and/or modality to one or more of vascular access ports 10, 10', 50, 60, and 70.

Vascular occluder 80 is shown in FIG. 10 in an elastically relaxed configuration wherein occluding section 84 forms a tubular bellows-like shaped structure comprising a plurality of bellows sections 86. From this state, occluding section 84 is elastically stretchable longitudinally into a delivery configuration (shown in FIG. 11A, for example) having a delivery length DLL and a delivery diameter DD, and elastically compressible longitudinally into a deployed configuration (shown in FIG. 11D, for example) having a deployed length DPL smaller than the delivery length DLL and a deployed diameter AD greater than delivery diameter DD. Deployed length is optionally about 50% or less than delivery length DLL. Delivery length DLL is optionally greater than about 10 mm, and the deployed length DPL is optionally smaller than about 6 mm, and delivery diameter DD is optionally smaller than about 1.5 mm with deployed diameter AD is optionally greater than about 3 mm.

Occluder body 81 (including occluding section 84) is formed of a braided or interwoven sleeve. The sleeve may be formed of metal wires such as Nickel-Titanium alloy wires, optionally about 20 to 200 wires, optionally of about 25 to about 70 micrometer in diameter each. The braid pattern may include a portion of wires of a radiopaque metal, optionally containing Platinum or Palladium, for improved visibility under fluoroscopic imaging. The braiding may be executed either manually or by using a braiding machine. Sleeve outer diameter may be constant in diameter and its size may vary and be approximated to average internal diameter of the target vessel. Following sleeve braiding, it can then undergo a shape setting treatment, bringing it to its resting (relaxed) state configuration. To accomplish that, the sleeve can be installed on a bellows-shaped mandrel of chosen shape and dimensions, forcing it to the desired shape, followed by annealing phase (which may include heating at a temperature of 500-650° C. for a duration of 2-15 minutes, for example, followed by a rapid cooling in water or oil). The braided sleeve may then undergo complimentary metallurgical treatments to improve its corrosion and fatigue resistance.

Vascular occluder 80 is configured such that, when occluding section 84 is in the deployed configuration, radially inner portions of the plurality of bellows sections 86 and/or of distal and proximal body ends 82 and 83 are fixedly pressed tight against each other parallel to the longitudinal axis 85. Vascular occluder 80 may be configured such that, when the occluding section 84 is in the deployed configuration, the radially inner portions are deformed into a condensed form with no gap therebetween. Furthermore, when occluding section 84 is in the deployed configuration, radially outer portions of the plurality of bellows sections 86 are optionally configured to be spaced radially outwardly from the radially inner portions, are allowed to shift relative to each other and/or to be arranged with gaps therebetween.

Occluding section 84 is configured to lock in the deployed configuration after having been compressed longitudinally thereto. The occluding section 84 is configured to lock (e.g., self-lock) in the deployed configuration when at least one of bellows sections 86 is held bent towards longitudinal axis 85, optionally particularly if bent towards proximal body end 83. When locked this way, at least one of the bellows sections 86 is held deformed such that a radially outer portion 87 thereof is bent towards longitudinal axis 85. In such or other embodiments, a length securing member (which may optionally include use of a tension member) is provided with or as part of vascular occluder 80, which is configured to lock occluding section 84, selectively or automatically, in the deployed configuration by resisting lengthwise changes from the deployed length DPL.

Vascular occluder 80 also includes a tension member 88 extending along occluding section 84 and connected with a distal end thereof to a distal end of occluding section 84 (in this example, it adjoins with distal body end 82). Tension member 88 is configured to facilitate selective longitudinal compression of occluding section 84 such as by applying tension (e.g., by pulling with sufficient force in a proximal direction) to tension member 88 when a proximal end of the occluding section (in this example, it adjoins with proximal body end 83) is pushed in a distal direction. The tension member 88 is optionally connectable to proximal end of occluding section 84 (e.g., to proximal body end 83) when it is in the deployed configuration, for preventing elongation of occluding section 84 from the deployed length DPL, and as such can serve as a length securing member or part in a length securing mechanism.

In some embodiments, occluding section 84 encloses a lumen 89 extending along the longitudinal axis 85 with tension member 88 extending therethrough. In some embodiments, tension member 88 is configured to separate or cut to a predetermined length, optionally when pulled by a force greater than a predetermined tension force. Tension member 88 may also be releasably fixated with the distal end thereof to the distal end of occluding section 84, and configured to disconnect therefrom, optionally when pulled by a force greater than a predetermined tension force.

Figures 11A, 11B, 11C, 11D:
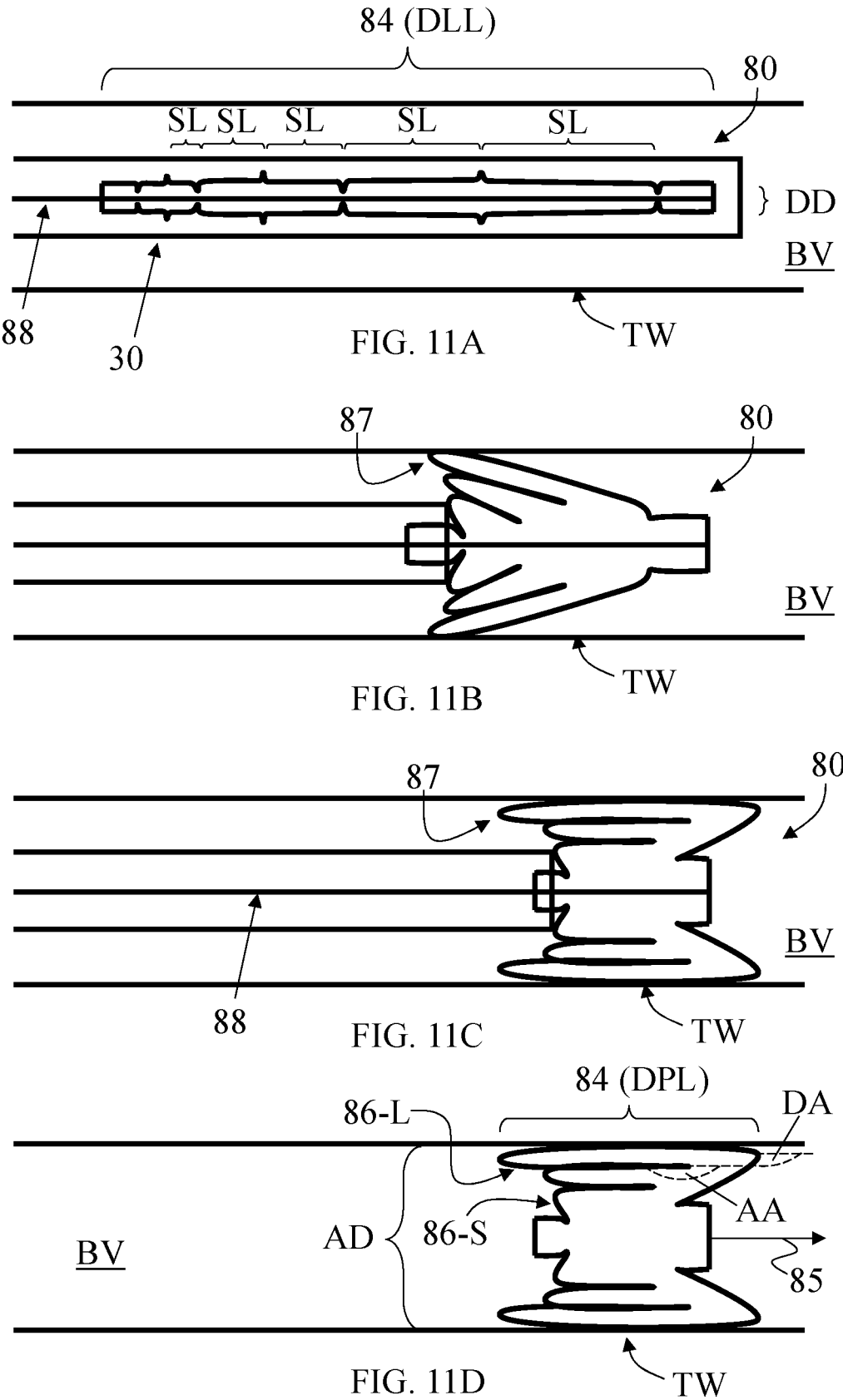
FIGS. 11A-11D schematically illustrate exemplary scenarios representing steps in an exemplary procedure for implanting the exemplary vascular occluder of FIG. 10, according to some embodiments.

Occluding section 84 is configured to reduce blood flow rate passing therethrough along the longitudinal axis 85 when compressing longitudinally to the deployed configuration shown in FIGS. 11C and 11D from a less elastically stressed longitudinally compressed state shown in FIG. 11B. Occluding section 84 is configured to increase in maximal outer diameter when compressing longitudinally to the deployed configuration from the less elastically stressed longitudinally compressed state. Furthermore, occluding section 84 is configured to increase in elastic resistance to radial compression, when compressing longitudinally to the deployed configuration, from the less elastically stressed longitudinally compressed state.

At least one of the plurality of bellows sections 86 extends between respective first 90 and second 91 inward creases, and comprises a respective frustum-shaped ascending portion 92 extending from the respective first inward crease 90 to a respective outward crease 93, and a respective frustum-shaped descending portion 94 extending from the respective outward crease 93 to the respective second inward crease 91. At least one of the respective frustum-shaped ascending portion 92 and frustum-shaped descending portion 94 is configured to reduce blood flow permeability therethrough along the longitudinal axis 85, when occluding section 84 changes to the deployed configuration.

In each pair of adjacent bellows sections 86 comprising of respective first and second bellows sections, the respective second inward crease 91 of the respective first bellows section and the respective first inward crease 90 of the second bellows section are adjoined circumferentially at a mutual curved or bent circumferential inner edge 95 having an inward apex 96 projecting radially-inwardly towards the longitudinal axis 85. The respective outward crease 93 includes a curved or bent circumferential outer edge 97 having an outward apex 98 projecting radially-outwardly from the longitudinal axis 85.

In some embodiments and as shown, at least some of the plurality of bellows sections 86 vary in enclosed largest diameter, and in at least one of the plurality of bellows sections 86 a smallest diameter enclosed by the respective second inward crease 91 is greater than a smallest diameter enclosed by the respective first inward crease 90 and smaller than a largest diameter enclosed by the outward crease 93. In some such embodiments, in each three sequentially positioned bellows sections of the plurality of bellows sections 86, comprising a respective second bellows section longitudinally positioned between a respective first bellows section and a respective third bellows section, the respective largest diameter enclosed by the respective second bellows section is equal to or greater than the respective largest diameter enclosed by the respective first bellows section and is equal to or smaller than the respective largest diameter enclosed by the respective third bellows section.

At least one of the plurality of bellows sections 86 is less permeable adjacent to respective first inward crease 90, second inward crease 91 and/or outward crease 93 than to remainder of the respective frustum-shaped ascending portion 92 and/or frustum-shaped descending portion 94, to blood flow passing therethrough along the longitudinal axis. As such, the regions at and adjacent to the creases are considered less permeable (or optionally impermeable) regions similar to regions 73 described above. In some embodiments and as shown, the different creases in each bellows section 86 and across most or all bellows sections 86 vary in radial location (e.g., distance) from longitudinal axis 85, therefore when occluding section 84 is longitudinally compressed in the deployed configuration, these less permeable regions causes immediate drop in permeability.

In some embodiments and as shown, the plurality of bellows sections 86 includes at least one larger bellows section 86-L having the respective outward crease 93 thereof enclosing a largest diameter greater than diameter of the treated bodily lumen portion, and at least one smaller bellows section 86-S having the respective outward crease thereof 93 enclosing a largest diameter equal to or smaller than diameter of the treated bodily lumen portion. As such, the radially outer portions of at least larger bellows section 86-L and smaller bellows section 86-S are considered anchoring portions similar to anchoring portions 61 described above. As such, vascular occluder 80 is configured such that when occluding section 83 is in the deployed configuration, the at least one smaller bellows section 86-S presses radially outwardly against the larger bellows section 86-L, thereby increasing anchoring pressure towards the blood vessel wall and/or increases resistance to radial inward compression.

In some embodiments and as shown, in at least one of the plurality of bellows sections 86 the respective frustrum-shaped ascending portion 92 is different in slant length SL than the respective frustum-shaped descending portion. Additionally or alternatively, at least some of the plurality of bellows sections 86 may vary in slant length SL of the respective frustum-shaped ascending portion 92 and/or frustum-shaped descending portion 94 thereof. Similarly, at least some of the plurality of bellows sections 86 vary in cumulative (total) slant length of the respective frustum-shaped ascending portion 92 and frustum-shaped descending portion 94 thereof.

The respective frustum-shaped ascending portion 92 forms an ascending angle AA with longitudinal axis 85 and the respective frustum-shaped descending portion 94 forms a descending angle DA, with and in the direction of longitudinal axis 85. In some embodiments and as shown, when the occluding section 84 is in the elastically relaxed configuration, ascending angle AA is smaller than 90° and descending angle DA is greater than 90°. When occluding section 84 is in the deployed configuration, each one of ascending angle AA and descending angle DA is either greater or smaller than 90° (in this example and as shown, both angles are greater than 90°).

A method of occluding a blood vessel BV may include a sequence or a number of steps that include one or more of the scenarios shown in FIGS. 11A-11D. Vascular occluder 80 is inserted into blood vessel BV proximately to a target wall portion TW of blood vessel BV when the occluding section 84 is held restrained in the delivery configuration (FIG. 11A). Delivery is performed using a delivery catheter such as catheter 30, and once in place the vascular occluder 80 is ejected from lumen of the delivery catheter (such as by using pusher 31), for allowing occluding section 84 to be released in blood vessel BV by shortening and expanding laterally into a less elastically stressed configuration (as shown in FIG. 11B). In some embodiments, occluding section 84 can be selectively maintained (e.g., manually or with a locking mechanism, for example) in the delivery configuration and in delivery length DLL also after partially or fully uncovering it from catheter 30, until the operator chooses to release and/or compress it to a smaller length. Alternatively, vascular occluder 80 can be operated (automatically or selectively) such that upon uncovering from catheter 30, occluding section 84 is immediately released, gradually during uncovering process or fully upon complete uncovering, into a less elastically stressed configuration, such as the one illustrated in FIG. 11B, for example.

As shown in FIG. 11C, occluding section 84 can then be compressed longitudinally by applying opposite forces to distal and proximal ends of occluding section 84 (optionally by pushing catheter 30 and/or pulling tension member 88) into the deployed configuration, thereby increasing longitudinal elastic stress of occluding section 84 relative to the less elastically stressed configuration. This forceful longitudinal compression, and in view of the diameter varying design of the bellows sections 86 described above, causes the at least one smaller bellows section 86-S to press radially outwardly against the larger bellows section 86-L thereby increasing grip and resistance to inward compression by the target wall portion TW.

The compression may also include or be accomplished by pressing tight radially inner portions of the plurality of bellows sections 86 and/or of the distal and proximal body ends 82 and 83 against each other parallelly to the longitudinal axis 85, which optionally causes reduced permeability of the occluding section 84 to blood flowing longitudinally therethrough. FIG. 11D shows vascular occluder 80 with occluding section locked in the deployed configuration, either due to its self-locking design once compressed in the deployed configuration (as shown), or when locked using a length securing member (as shown in FIG. 1C, for example).

Releasing or compressing longitudinally occluding section 84 as described forces bending of at least one of the bellows sections 86 towards the longitudinal axis 85, and then the compressing longitudinally or locking generates continuous internal stresses configured to hold the at least one of the bellows sections 86 bent towards the longitudinal axis 85, thereby locking occluding section 84 in the deployed configuration.

In case the locking includes use of tension member 88, a portion thereof can be connected to a proximal end of occluding section 84 when in the deployed configuration, and the remainder portion of tension member 88 proximally to occluding portion 84 can be disjoined or cut, optionally to a predetermined length, such as by applying tension thereto above a chosen tension force. Alternatively, in case tension member 88 is not used for holding occluding section 84 locked but only for applying compression thereto, the step of locking occluding section 84 can be followed by releasing or disconnecting tension member 88 from the distal end of occluding section 84, such as by cutting and/or by applying tension thereto above a chosen tension force.

In some embodiments, the occluding section of the vascular occluder is less permeable to blood flowing therethrough when in the deployed configuration relative to when in the elastically relaxed configuration. The flow obstruction portions may be at least partially permeable to blood flowing therethrough, and in some such embodiments the occluding section also includes an impermeable portion configured to block blood from flowing through the occluding section along the longitudinal axis, when in the deployed configuration. In some embodiments, the impermeable portion is not completely impermeable but characterized with substantially low permeability and/or substantially more thrombogenic than other portions of the occluding sections.

The impermeable portion may include, or be configured as, a coating of inner or outer portions of the occluding sections and/or a radially expandable member housed in the occluding section between the flow obstruction portions. Alternatively, the impermeable portion may include, or be configured as, an at least one axially extendable-compressible member extending through the occluding section and configured to allow unhindered stretching of the occluding section to the delivery configuration, and to compress into a flattened or condensed form spanning over part or substantially all axial cross-sectional area of the occluding section when in the deployed configuration thereby occluding the occluder body. In some such embodiments, the impermeable portion may be configured to allow blood flow through the occluding section when in the elastically relaxed configuration.

FIGS. 12A-12C schematically illustrate side cross-sectional views of a vascular occluder 100 comprising an exemplary impermeable portion configured as an axially extendable-compressible occlusion member 101. Vascular occluder is shown respectively in a delivery configuration (FIG. 12A), in an elastically relaxed configuration (FIG. 12B) and in a deployed configuration (FIG. 12C). Vascular occluder 100 may be an exemplary implementation or variation of vascular access port 10, 10', 50, 60, 70 and/or 80, and/or it may include some or all embodiments and features of vascular access port 10, 10', 50, 60, 70 and/or 80, and/or be identical or similar in function, structure and/or modality to one or more of vascular access ports 10, 10', 50, 60, 70, and 80. Vascular occluder 100 includes a tension member 102 and an elongated occluding body 103 comprising a distal body end 104, a proximal body end 105 and an occluding section 106 extending longitudinally between distal body end 104 and proximal body end 105. Occluding section 106 in the elastically relaxed configuration is elastically stretchable longitudinally to the delivery configuration having a delivery length and a delivery diameter, and is elastically compressible longitudinally to a fixed deployed configuration having a deployed length smaller than the delivery length and a deployed diameter greater than the delivery diameter. When occluding section 106 in the elastically relaxed configuration, it forms a tubular bellows-like shaped structure comprising a plurality of bellows sections, in this example three bellows sections as shown.

Occluding section 106 includes is at least partially permeable to blood flowing therethrough when occluding section 106 is in a more elastically relaxed longitudinally, or when in the elastically relaxed configuration, than when in the deployed configuration. In some embodiments, occluding section 106 is still permeable to blood flow even when it is tightly compressed in the deployed configuration. In order to achieve immediate occlusion when in the deployed configuration, occluding section 106 further includes occlusion member 101, formed of a material impermeable to blood, and configured to compress into a flattened or condensed form spanning over most or all axial cross section of occluding section 106 when in the deployed configuration, thereby occluding occluder body 100 and the passage it is implanted in.

Occlusion member 101 is optionally connected to occluder body 103, optionally with one end thereof connected to a distal portion of occluding section 106 and with its other end to a proximal portion of occluding section 106, or it may be unconnected and allowed to 'float' within boundaries of occluding section 106, such that it extends along some, most or all length of occluding section 106. When in the elastically relaxed configuration, occlusion member 101 may take a spiral form such that it can stretch sufficiently to allow unhindered extension of occluding section 106 to the delivery configuration. The spiral form may vary in diameter, optionally similarly to conical or frustum spiral, so that when occlusion member 101 is compressed within occluding section 106 being tightly compressed in the deployed configuration, it will substantially seal or span most or entire cross-sectional area of occluding section 106. Occlusion member 101 may include an elastic slender core member covered or encapsulated with a wider soft or malleable impermeable material, for example the core member is formed of Ni—Ti alloy and the covering material includes a strip of cloth or soft polymer, having a width being optionally equal to or smaller than maximal diameter of occluding section 106, and/or optionally greater than half the maximal diameter of occluding section 106, when in the deployed configuration.

Figures 13A, 13B, 14, 15:
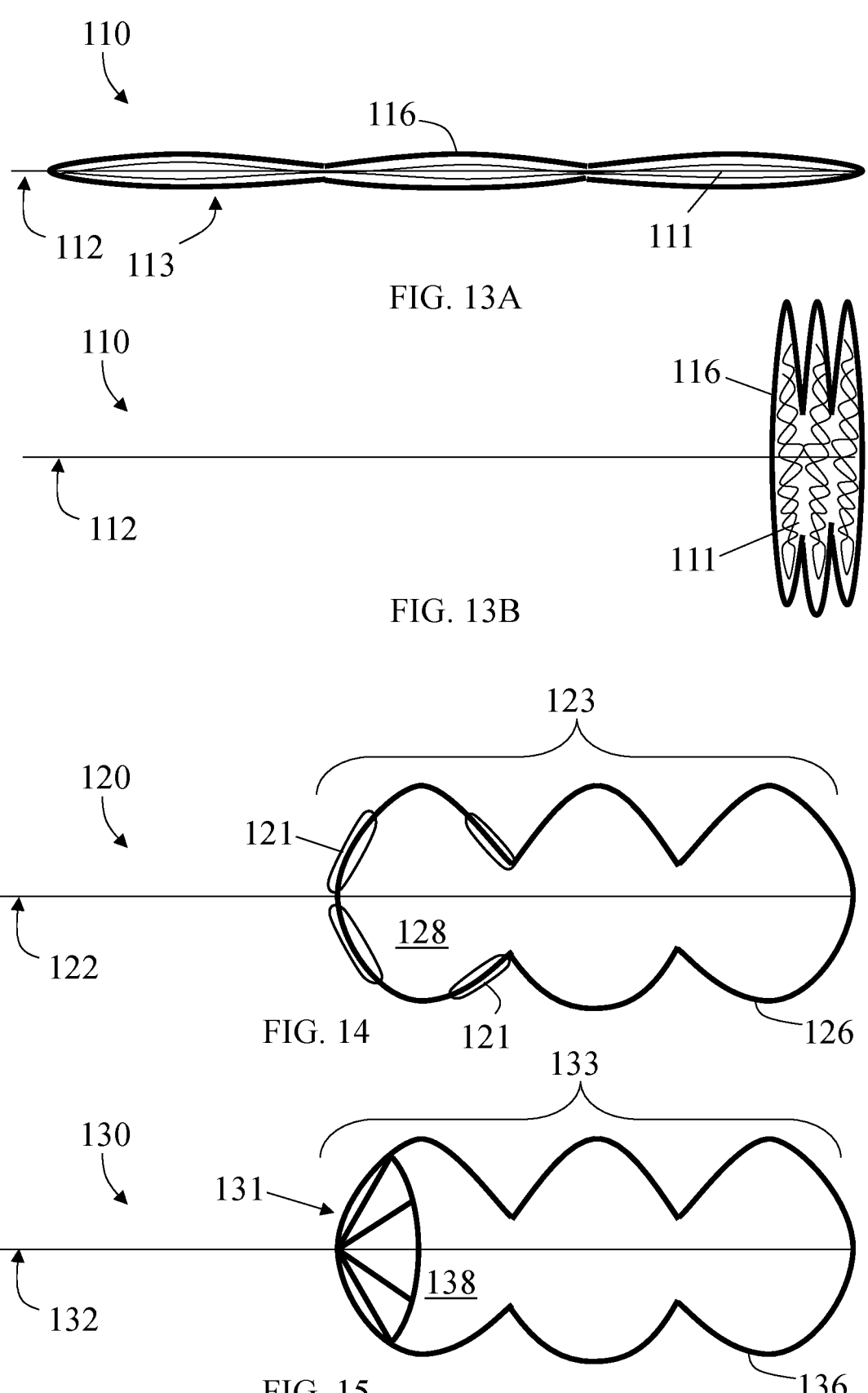
FIGS. 13A-13B schematically illustrate an exemplary vascular occluder comprising a second exemplary impermeable portion, shown respectively in a delivery configuration and in a deployed configuration, according to some embodiments.
FIG. 14 schematically illustrate an exemplary vascular occluder comprising a third exemplary impermeable portion shown in a deployed configuration, according to some embodiments.
FIG. 15 schematically illustrate an exemplary vascular occluder comprising a fourth exemplary impermeable portion shown in a deployed configuration, according to some embodiments.

FIGS. 13A-13B schematically illustrate side cross-sectional views of a vascular occluder 110 comprising an exemplary impermeable portion configured as a plurality of slender occlusion members 111. Vascular occluder 110 is shown respectively in a delivery configuration (FIG. 13A), and in a deployed configuration (FIG. 13B). Vascular occluder 110 may be an exemplary implementation or variation of vascular access port 10, 10'. 50, 60, 70 and/or 80, and/or it may include some or all embodiments and features of vascular access port 10, 10', 50, 60, 70 and/or 80, and/or be identical or similar in function, structure and/or modality to one or more of vascular access ports 10, 10', 50, 60, 70, and 80. Vascular occluder 110 includes a tension member 112 and an elongated occluding body 113 comprising an occluding section 116 extending longitudinally between distal and ends of occluding body 113. Occluding section 116 in the elastically relaxed configuration is elastically stretchable longitudinally to the delivery configuration having a delivery length and a delivery diameter and is elastically compressible longitudinally to a fixed deployed configuration having a deployed length smaller than the delivery length and a deployed diameter greater than the delivery diameter. When occluding section 116 in the elastically relaxed configuration, it forms a tubular bellows-like shaped structure comprising a plurality of bellows sections, in this example three bellows sections as shown.

Occluding section 116 is at least partially permeable to blood flowing therethrough when in a more elastically relaxed longitudinally, or when in the elastically relaxed configuration, than when in the deployed configuration. In some embodiments, occluding section 116 is still permeable to blood flow even when it is tightly compressed in the deployed configuration. In order to expedite or cause immediate occlusion when in the deployed configuration, occluding section 116 further includes a plurality of occlusion members 111 formed of a material configured to enhance clot formation and/or impermeable to blood flow. As such, occlusion members 111 are configured to jointly compress into a flattened or condensed form spanning over most or all axial cross section of occluding section 116, and/or fill most or all space within occluding section 116, when in the deployed configuration, thereby occluding occluder body 110 and the passage it is implanted in.

Each one of occlusion members 111 may be disconnected and allowed to 'float' within boundaries of occluding section 116, or be connected to occluding section 116 such as with one end thereof to a distal portion of occluding section 116 and with its other end to a proximal portion of occluding section 116, such that it extends along some, most or all length of occluding section 116. When in the elastically relaxed configuration, occlusion members 111 may take a loose form such that it can extend to a tighter form sufficiently to allow unhindered extension of occluding section 116 to the delivery configuration. The occlusion members 111 may vary in length and/or relative height or distance from longitudinal axis of occluding section 116, so that when occlusion members 111 are compressed or condensed within occluding section 116 being tightly compressed in the deployed configuration, it will substantially seal or span the entire cross-sectional area and/or volume of occluding section 116. Each one of occlusion members 111 may include a soft or malleable impermeable material, optionally formed of fibers or a strip of cloth or soft polymer.

FIG. 14 schematically illustrate side cross-sectional view of a vascular occluder 120, shown in an elastically relaxed configuration, comprising an exemplary impermeable or less permeable portion configured as one or more areas of impermeable coating 121. Vascular occluder 120 may be at least partially identical or similar in function, structure and/or modality to one or more of vascular access ports 10, 10', 50, 60, 70, and 80. Vascular occluder 120 includes a tension member 122 and an elongated occluding body 123 and an occluding section 126 extending longitudinally between distal and proximal ends of occluding body 123. When occluding section 126 in the elastically relaxed configuration, it forms a tubular bellows-like shaped structure comprising a plurality of bellows sections, in this example three bellows sections as shown.

Impermeable coating 121 covers one or more surface areas of occluding section 126, optionally at least (e.g., only) in proximal-most bellows section 128 thereof. Impermeable coating 121 is optionally formed thin sheets of PTFE, EPTFE and/or polyurethane derivative, optionally about 10 μm or less, optionally by way of electrospinning. Impermeable coating 121 is optionally formed in a dome shape with a hole at its center to allow unhindered axial motion of tension member 122, and it may also cover portions of one or more creases of occluding section 126, thus covering the cross-sectional area thereof when in the deployed configuration. In some embodiments, impermeable coating 121 does not cover radially outward (peripheral) portion(s) of proximal-most bellows section 128, including outward crease thereof, which is configured to directly engage with, and optionally contour and conform to size and shape of the treated bodily passage, so it is configured to be already pressed tight and therefore optionally impermeable while the coating may interfere with this function. In some embodiments, impermeable coating 121 does not cover radially inward (peripheral) portion(s) of proximal-most bellows section 128 including inward crease thereof.

FIG. 15 schematically illustrate side cross-sectional view of a vascular occluder 130, shown in an elastically relaxed configuration, comprising an exemplary impermeable portion configured as a radially expandable member 131. Vascular occluder 130 may be an exemplary implementation or variation of vascular access port 10, 10', 50, 60, 70 and/or 80, and/or it may include some or all embodiments and features of vascular access port 10, 10', 50, 60, 70 and/or 80, and/or be identical or similar in function, structure and/or modality to one or more of vascular access ports 10, 10', 50, 60, 70, and 80. Vascular occluder 130 includes a tension member 132 and an elongated occluding body 133 comprising an occluding section 136 extending longitudinally between distal and proximal ends thereof. When occluding section 136 in the elastically relaxed configuration, it forms a tubular bellows-like shaped structure comprising a plurality of bellows sections, in this example three bellows sections as shown. Radially expandable member 131 is housed within occluding section 136, optionally at least (e.g., only) in proximal-most bellows section 138 thereof, and it is configured to cover and/or seal one or more surface areas of occluding section 136 when in the deployed configuration.

Radially expandable member 131 optionally comprises a folding canopy or umbrella-like mechanism comprising support ribs covered in a dome shape elastic and/or malleable membrane with a hole at its center to allow unhindered axial motion of tension member 132. The supporting ribs bay be coupled or otherwise integrated with occluding section 136 to control its activation. The membrane may be formed of electrospun polyurethane or PTFE derivative, and the ribs may be formed of metallic (e.g., Ni—Ti alloy) or polymeric wires. Membrane may be about 10 μm or less thick also for facilitating effective folding and accommodation within occluding section 136 when in the delivery configuration. In some embodiments, radially expandable member 131 does not cover radially outward (peripheral) portion(s) of proximal-most bellows section 138, including outward crease thereof. In some embodiments, radially expandable member 131 does not cover radially inward (peripheral) portion(s) of proximal-most bellows section 138 including inward crease thereof.

Figures 16A, 16B:
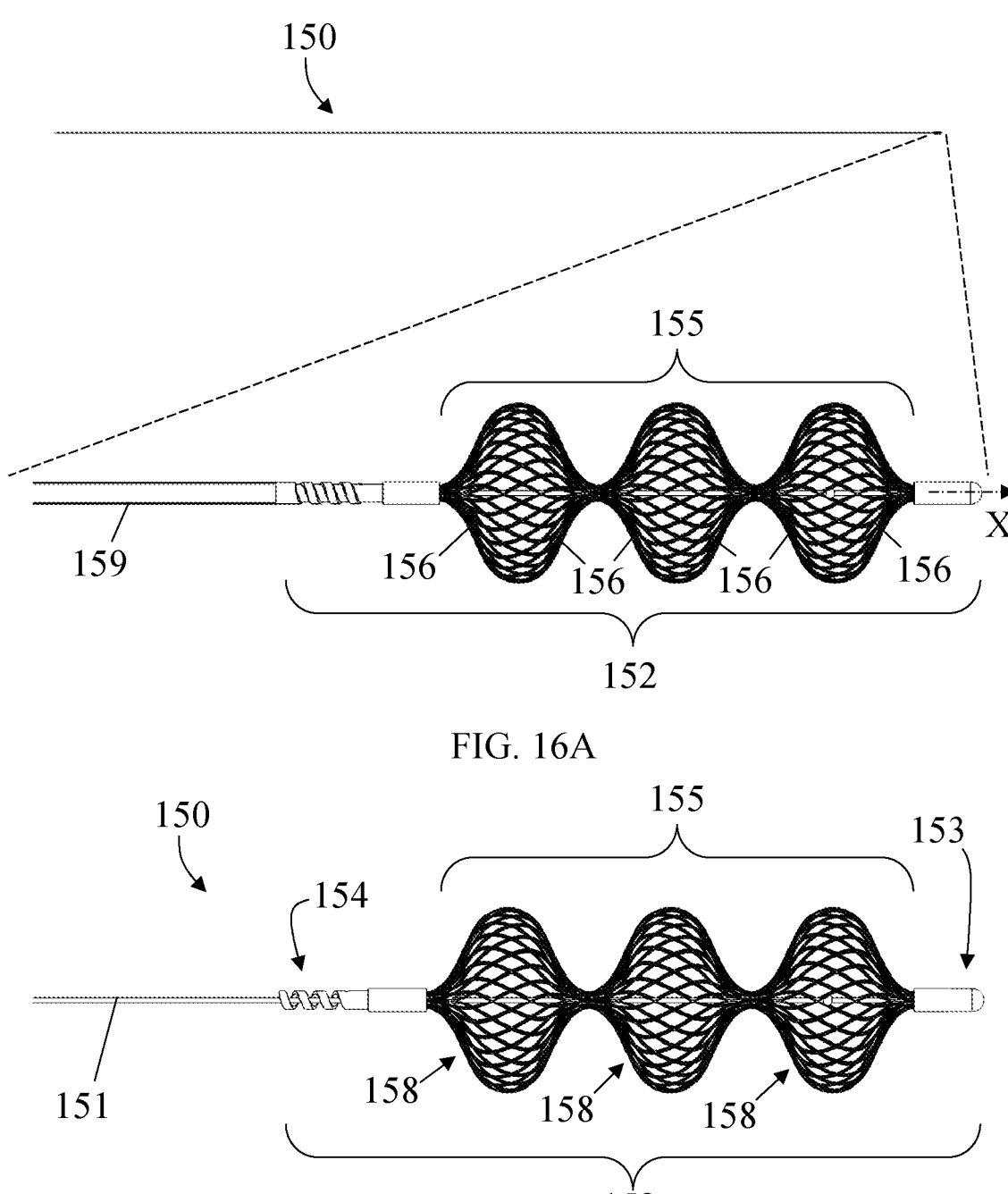
FIGS. 16A-16B illustrate side views of an exemplary vascular occluder before and after disconnection and removal of a pusher, according to some embodiments.
Figure 17A:
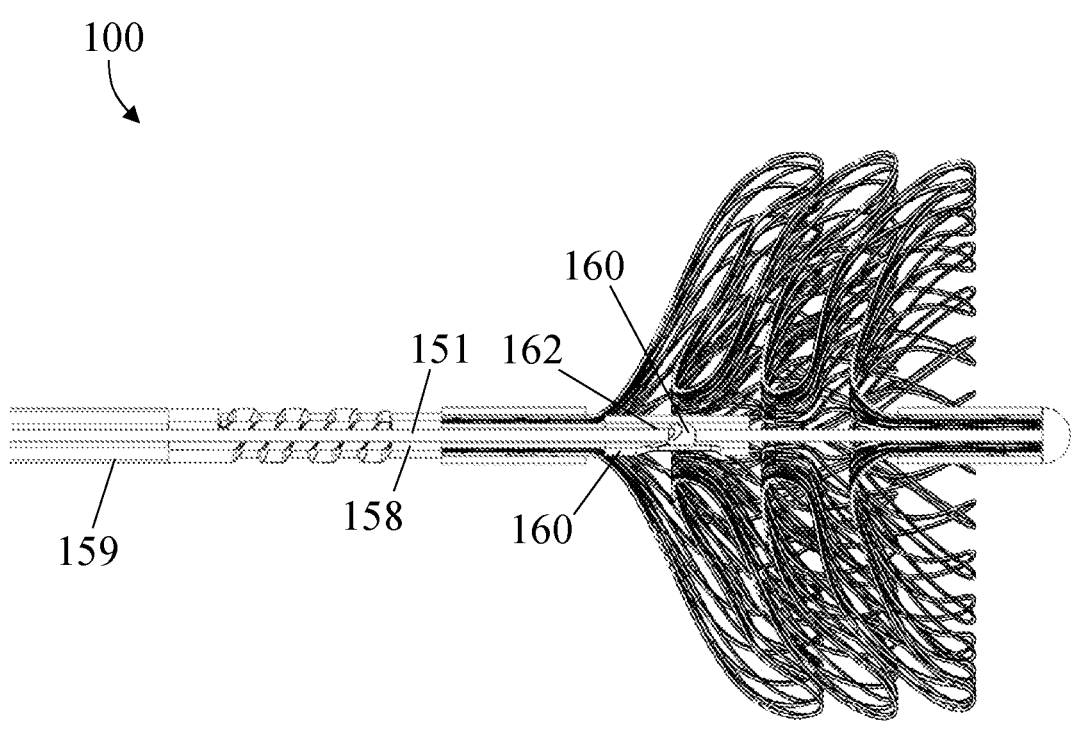
FIGS. 17A-17B illustrate enlarged side cross-sectional views of a distal portion of the exemplary vascular occluder of FIG. 16A, according to some embodiments.
Figure 17B:
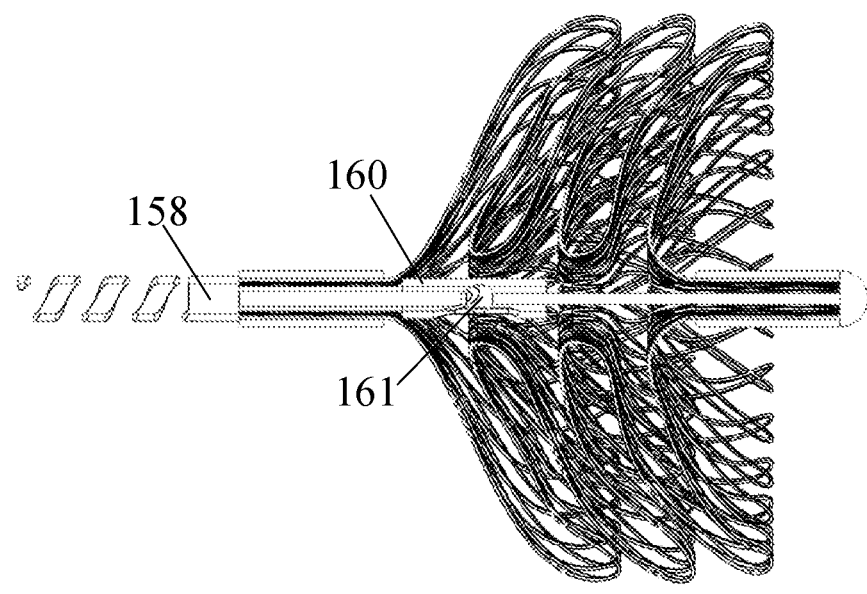

FIGS. 16A-16B illustrate an exemplary vascular occluder 150, configured for occluding a bodily lumen portion or passage, and which may be an exemplary implementation or variation of vascular access port 10, 10', 50, 60, 70 and/or 80, and/or it may include some or all embodiments and features of vascular access port 10, 10', 50, 60, 70 and/or 80, and/or be identical or similar in function, structure and/or modality to one or more of vascular access ports 10, 10', 50, 60, 70, and 80. FIGS. 17A-17B illustrate enlarged side cross-sectional views of a distal portion of vascular occluder 150, and FIGS. 18A-18D schematically illustrate exemplary scenarios representing steps in an exemplary procedure for occluding blood vessel BV using vascular occluder 150.

Vascular occluder 150 includes a tension member 151, and an elongated occluder body 152 comprising a distal body end 153, a proximal body end 154 and an occluding section 155 extending along a longitudinal axis X between distal body end 153 and proximal body end 154. Occluding section 155 includes a plurality of flow obstruction portions 156 provided sequentially along a portion of tension member 151 and extending at least partially transversely thereto. Tension member 151 passes through a respective lumen 157 of each one of flow obstruction portions 156 such that one or more of them can be moved axially over tension member 151 relatively to remainder of flow obstruction portions 156. Occluding section 155, when in an elastically relaxed configuration as shown, forms a tubular bellows-like shaped structure comprising a plurality of bellows sections 158, and is elastically stretchable longitudinally to a delivery configuration (shown in FIG. 18A) having a delivery length DLL and a delivery diameter, and elastically compressible longitudinally to a fixed deployed configuration (shown in FIG. 18D) having a deployed length DPL smaller than delivery length DLL and a deployed diameter greater than the delivery diameter. Deployed length DPL, which is optionally smaller than 6 mm, is about 50% or less than delivery length DLL being optionally greater than 10 mm. The delivery diameter is optionally smaller than 1.5 mm and the deployed diameter is optionally greater than 3 mm. Occluding section 155 is formed of a braided sleeve configured to increase in maximal outer diameter and in elastic resistance to radial compression when compressing longitudinally to the deployed configuration from a less elastically stressed longitudinally compressed state.

Vascular occluder 150 also includes an elongated pusher 159 which is selectively detachable from occluder body 152 following deployment thereof. Vascular occluder 150 is sized and configured to pass through a lumen of a catheter (e.g., catheter 30) when occluding section 155 is in the delivery configuration, by way of advancing pusher 159 distally with occluder body 152 at least until occluding section 155 is partially or entirely protruding via a distal opening of catheter lumen, with pusher 159 and tension member 151 being sufficiently long for extending along the catheter lumen and through a proximal opening thereof. Occluding section 155 can be changeable from the delivery configuration to the elastically relaxed configuration, when entirely protruding via the distal catheter opening. In situations where tension member 151 is taut during delivery through the catheter, it should be ensured that tension is sufficiently reduced and/or that tension member 151 is allowed to be sufficiently loose for allowing the more elastically relaxed configuration of occluding section 155. In some embodiments, tension member 151 is originally set to allow unhindered stretching of occluding section 155 to the delivery length with minimal to no tension thereon, and when occluding section 155 protrudes distally from the catheter, it self-contracts to a less elastically stressed form or to the elastically relaxed configuration. Occluding section 155 can then be selectively changed from the elastically relaxed configuration to the deployed configuration by applying tension in tension member 151, optionally above a predetermined value, sufficiently to compress and lock occluding section 155 in the deployed configuration, optionally being greater than about 0.1 Newton (N), optionally greater than about 0.5 N, optionally greater than about 1 N, or any intermediate value therebetween.

Vascular occluder 150 includes a length securing member 160 configured to engage with an enlarged or wide portion 161 of tension member 151 and to lock occluding section 155 in the deployed configuration by resisting wide portion 161 retraction therefrom, therefore preventing occluding section 155 from elongating from the fixed deployed length. Occluding section 155 is configured to lock in the deployed configuration after having been compressed longitudinally into the deployed configuration, optionally when bellows sections 158 are at least partially fitting and/or nesting within each other, optionally such that at least one of the bellows sections is held bent towards distal body end 153. Tension member 151 is configured to cut to a predetermined length, using cutting element 162 connected to occluder body 152 proximally to length securing member 160, when tension member 151 is pulled by a force greater than a predetermined value optionally greater than about 1 N, optionally greater than 2 N, or of any intermediate value.

Vascular occluder 150 is configured such that, when occluding section 155 is in the deployed configuration, radially inner portions of bellows sections 158 are fixedly pressed tight and/or condensed against each other parallel to longitudinal axis X, while radially outer portions of bellows sections 158, spaced radially outwardly from the radially inner portions, are looser and allowed to shift relative to each other so as to form the nested configuration of occluding section 155 as shown in FIG. 17 for example.

Figures 18A, 18B, 18C, 18D:
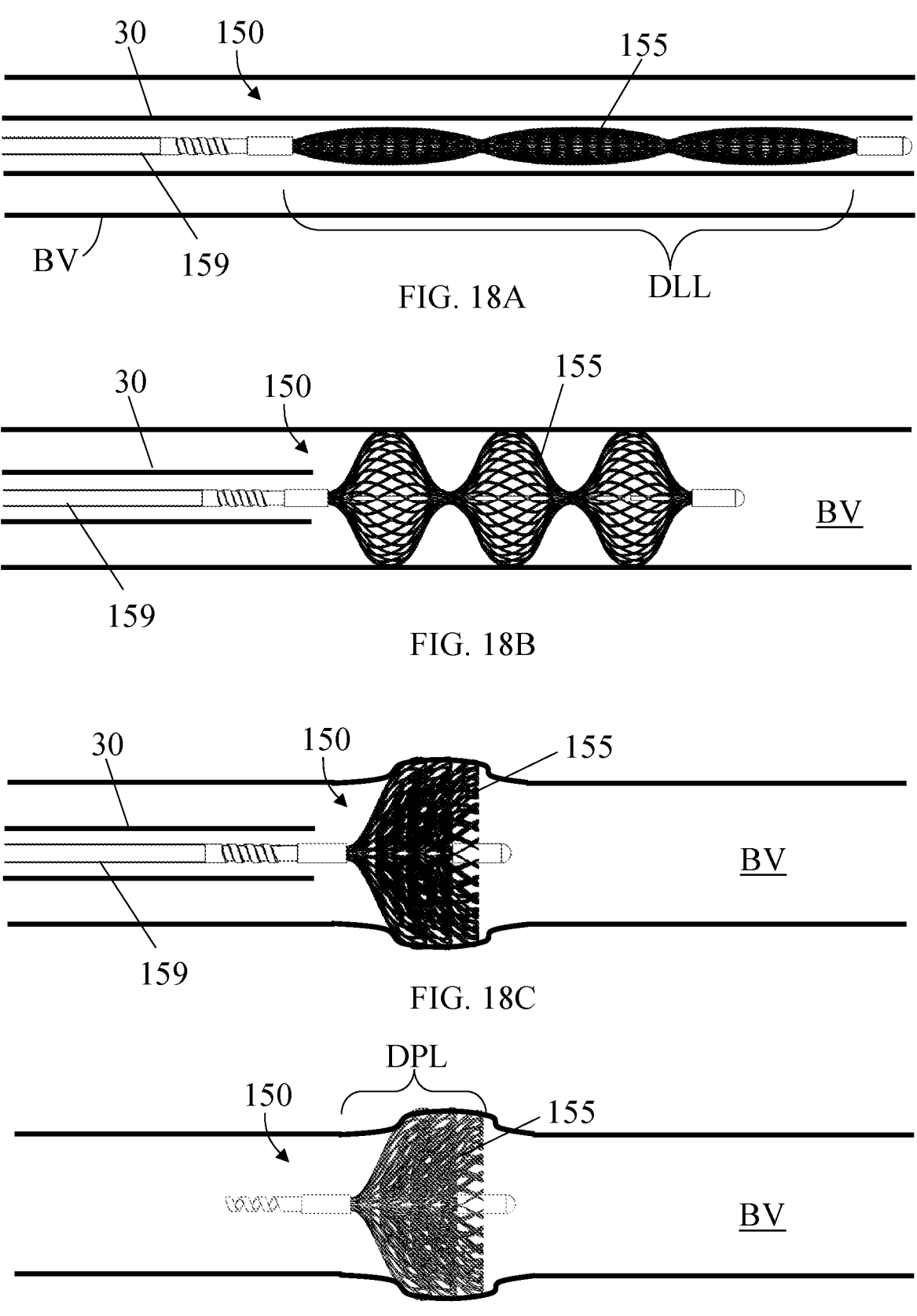
FIGS. 18A-18D illustrate exemplary scenarios representing steps in an exemplary procedure for occluding a blood vessel using the exemplary vascular occluder of FIG. 16A, according to some embodiments.

Vascular occluder can be used for occluding (i.e., block or substantially reduce blood flow in) a passage in a body of a live subject, such as blood vessel BV. As shown in FIG. 18A, vascular occluder 150 is inserted into blood vessel BV via catheter 30, using pusher 159 connected thereto, while maintaining occluding section 155 stretched in the delivery configuration. This is optionally achieved by the dimensional constraints of catheter 30 lumen, or occluding section 155 can first be locked in a stretched mode before insertion to, and delivery via, catheter 30. In any event, tension member 151 is allowed to extend to up to a maximally allowed length between distal body end 153 and proximal body end 154 for facilitating unhindered stretching of occluding section 155 to the delivery configuration.

Once in a chosen target location in blood vessel BV, occluding section 155 is protruded distally entirely from within catheter 30 using pusher 159 and/or by withdrawing catheter 30 relative thereto, as shown in FIG. 18B. Occluding section 155 is then released in blood vessel to shift from the delivery configuration such is forced manually or allowed to autonomously shorten and expand laterally into a less elastically stressed configuration. Occluding section 155 can recover to the elastically relaxed configuration if blood vessel BV inner diameter is sufficiently large at the occlusion site, otherwise the achieved less elastically stressed configuration engages with blood vessel walls and restricted to conform at least partially to blood vessel BV boundaries imposed thereto.

Vascular occluder 150 can be checked under imaging, and be slightly shifted, maneuvered and/or twisted as needed until it is in a chosen position and orientation, and it can also be retracted back into catheter 30 while reversing to the delivery configuration and be repositioned in blood vessel BV or completely withdrawn, for example. For local occlusion of blood vessel BV simultaneously with vascular occluder 150 anchoring to surrounding wall of blood vessel BV, occluding section 155 is forced to compress longitudinally until meeting the deployed configuration as shown in FIG. 18C, by increasing longitudinal elastic stress of occluding section 155 relative to the less elastically stressed configuration. This is achieved by holding pusher 159 in place while pulling tension member 151, or the other way around. In some embodiments, compressing occluding section 155 causes significant local expansion of blood vessel BV thereby decreasing blood flow rate, average velocity and/or flux, locally, to a sufficient degree known to naturally generate thrombus and subsequently vessel occlusion. In some embodiments, the operator can determine, in advance or during operation under imaging, one parameter or more (such as occluder size, degree of expansion, time of expansion or others) to increase local diameter or cross-sectional area of blood vessel BV to a degree sufficient to cause localized decrease on flow rate such as to less than about 50%, optionally less than about 25%, optionally less than about 5% the original flow rate.

By applying sufficient tension in tension member 151, over a predetermined value, optionally greater than about 1 N, optionally greater than about 2 N, or of any intermediate value, occluding section 155 is configured lock in the deployed configuration and deployed length DPL by length securing member 160, and tension member 151 is configured to be cut with cutting element 162. Once vascular occluder 150 is locked, anchored with tension member 151 cut to chosen length, pusher 159 can be disconnected from occluder body 152, and removed from blood vessel BV with catheter 30, as shown in FIG. 18D.

Following are various illustrative examples, each of which is a separate embodiment. This disclosure further includes all permutations of the "independent" examples below with their "dependent" examples. Moreover, additional embodiments capable of derivation from the independent and dependent examples that follow are also expressly incorporated into the present written description.

EXAMPLES

Example 1

A vascular occluder can comprise an elongated occluder body comprising a distal body end, a proximal body end; an occluding section extending between the distal body end and the proximal body end, longitudinally compressible along a longitudinal axis; and a tension member extending along the occluding section and connected with a distal end thereof to a distal end of the occluding section.

In some embodiments, the tension member is configured to facilitate selective longitudinal compression of the occluding section by applying tension to the distal end of the occluding section via the tension member while pushing distally a proximal end of the occluding section. In some embodiments, the occluder body is longitudinally stretchable to a delivery length wherein the occluding section is configured for passing unhinderedly through a catheter into a target blood vessel. In some embodiments, the occluder body is longitudinally compressible to a deployed length thereby radially extending with one or more anchoring portions thereof to a deployed diameter greater than diameter of the target blood vessel, wherein the occluding section is configured to limit or block blood from flowing therethrough.

In some embodiments, the occluding section is configured as a bellows-like structure comprising a plurality of tubular folds, each fold comprising at least one flow obstructing portion configured to limit or block blood from flowing therethrough.

In some embodiments, when the occluder body is in the delivery length the at least one flow obstructing portion extend substantially parallel to the longitudinal axis, and when the occluder body is in the deployed length the at least one flow obstructing portion extend transversally to the longitudinal axis.

In some embodiments, when the occluder body is in the deployed length, the occluding section is configured such that radially inner portions of the plurality of tubular folds and/or of distal and proximal body ends are fixedly pressed tight against each other parallel to the longitudinal axis.

In some embodiments, the occluder body includes a braided portion interbraided from at least one wire and configured to expand in diameter when compressed longitudinally.

In some embodiments, the occluder body is formed of a braided or interwoven sleeve.

In some embodiments, the tension member is configured as or comprising a length securing member configured to resist lengthwise changes from the deployed length of the occluder body.

In some embodiments, the length securing member is part of a locking mechanism and is provided at one end of the occluder body and configured to engage and selectively connect to a mating portion or member provided at another end of the occluder body, when the occluder body is in the deployed length.

In some embodiments, the length securing member is configured as a plastically deformable element, such as a wire, configured to plastically deform when the occluder body is compressed longitudinally from the delivery length to the deployed length and/or when the occluder body is forced to change in length from the deployed length.

In some embodiments, the length securing member is configured as an elastically deformable element, such as a wire, configured to elastically relax when the occluder body is compressed longitudinally from the delivery length to the deployed length and/or to elastically resist a change in length of the occluder body from the deployed length.

In some embodiments, the plurality of tubular folds comprising consecutive pairs of ascending portions and descending portions, each ascending portion and/or descending portion extends between respective outward apex projecting away from the longitudinal axis and inward crease projecting towards the longitudinal axis.

In some embodiments, each one of the plurality of tubular folds includes one of the anchoring portions adjacent to the outward apex thereof.

In some embodiments, the occluder body is configured such that the anchoring portions are forced to expand in diameter sufficiently for engaging with and/or pressing against a target wall portion of a blood vessel, laterally outwardly to the longitudinal axis, for fixating the at least one flow obstructing portion to the target wall portion.

In some embodiments, the ascending and/or descending portion in each one of the tubular folds includes one of the flow obstructing portion.

In some embodiments, the vascular occluder is configured such that a plurality of the flow obstructing portion are distant with each other when the occluder body is in the delivery length and are compressed against each other when the occluder body is in the deployed length.

In some embodiments, the plurality of the flow obstructing portion is configured to obstruct blood flow therethrough when the occluder body is in the deployed length or to allow a smaller rate of blood flowing therethrough than when the occluder body is in the delivery length.

In some embodiments, the occluder body, when in the deployed length, is configured such that the radially inner portions of the plurality of folds are deformed into a condensed form with no gap therebetween.

In some embodiments, each one of the radially inner portions is closer to the respective inward crease than to the respective outward apex, in each one of the plurality of folds.

In some embodiments, the occluder body, when in the deployed length, is configured such that radially outer portions of the plurality of folds spaced radially outwardly from the radially inner portions are allowed to shift relative to each other and/or to be arranged with gaps therebetween.

In some embodiments, the occluder body in the deployed length is thinnest adjacent to the radially inner portions and gradually increasing in thickness radially outwardly to the radially inner portions.

In some embodiments, the vascular occluder is configured such that a plurality of the flow obstructing portion are distant with each other when the occluder body is in the delivery length, thereby allowing a first rate of blood flow therethrough, and are compressed against each other when the occluder body is in the deployed length thereby blocking blood from flowing therethrough or allowing a second rate of blood flow therethrough smaller than the first rate.

In some embodiments, each one of the flow obstruction portion is formed at least partly from a mesh configured for allowing limited blood flow therethrough and/or for accumulating emboli in the occluder body and/or in mesh openings thereof.

In some embodiments, the delivery length is greater than 10 mm and/or the deployed length is smaller than 6 mm.

In some embodiments, the deployed length is about 50% or less than the delivery length.

In some embodiments, a maximal outer diameter of the occluder body is smaller than 1.5 mm when the occluder body is in the delivery length and greater than 3 mm when the occluder body is in the deployed length.

In some embodiments, a ratio of maximal outer diameter to length of the occluder body is smaller than 0.05 when the occluder body is in the delivery length and greater than 0.5 when the occluder body is in the deployed length.

In some embodiments, the occluding section encloses a lumen extending along the longitudinal axis, wherein the tension member passing through the lumen, wherein the occluder body is longitudinally compressible from the delivery length to the deployed length along the tension member.

In some embodiments, when the occluder body is in the delivery length, the occluding section is configured in a cylindrical-like form having a delivery diameter substantially constant along the longitudinal axis, and, when the occluder body is in the deployed length, the occluding section is configured such that each one of the tubular folds is expanded to an anchoring diameter adjacently to the outward apex thereof, such that the tubular folds collectively apply an anchoring force sufficient for facilitating engaging and pressing against a target wall portion of a blood vessel, laterally outwardly to the longitudinal axis, for fixating the at least one flow obstructing portion to the target wall portion.

In some embodiments, the delivery diameter is equal to or smaller than 1.5 mm, optionally particularly equal to or smaller than 0.5 mm.

In some embodiments, the anchoring diameter is equal to or greater than 3 mm, optionally particularly equal to or greater than 7 mm.

In some embodiments, the anchoring force is equal to or greater than 400 gr.

In certain embodiments, there is provided a method of occluding a blood vessel, the method comprising: inserting the vascular occluder into the blood vessel proximately to a target wall portion of the blood vessel; compressing longitudinally the plurality of tubular folds such that the flow obstruction portions thereof are adjacent and/or parallel to each other; and pressing tight radially inner portions of the plurality of tubular folds and/or of the distal and proximal body ends against each other parallelly to the longitudinal axis.

In some embodiments, the pressing tight includes allowing radially outer portions of the plurality of tubular folds spaced radially outwardly from the longitudinal axis to shift relative to each other and/or to arrange with gaps therebetween.

In some embodiments, the compressing longitudinally includes fixating the at least one flow obstructing portion to the target wall portion with outward apexes of the plurality of tubular folds.

In some embodiments, the inserting includes positioning a distal-most one of the flow obstructing portion adjacent to the target wall portion of the blood vessel, and the fixating includes pushing a proximal-most one of the flow obstructing portion towards the distal-most flow obstructing portion.

In some embodiments, the compressing longitudinally is configured to cause blocking of blood from flowing, or reducing rate of blood flow, through the flow obstructing portions.

In some embodiments, the compressing longitudinally and/or the pressing tight includes applying tension to the distal end of the occluding section via the tension member while pushing distally a proximal end of the occluding section.

In some embodiments, the pushing distally is applied directly to and/or across the radially inner portions.

In some embodiments, the inserting including ejecting a distal-most one of plurality of tubular folds into a space formed by an aneurism opened to the blood vessel distally to a neck portion of the aneurism adjoining the blood vessel, and ejecting a proximal-most one of the plurality of tubular folds in the blood vessel proximally to the neck portion.

In some embodiments, the pressing tight includes locking the vascular occluder to the neck portion by pressing the distal-most one of the plurality of tubular folds against the distal-most one of the plurality of tubular folds across the neck portion.

In some embodiments, the compressing longitudinally includes pulling proximally the distal end of the occluding section with the tension member against the neck portion and/or pushing distally the proximal end of the occluding section against the neck portion.

In some embodiments, the pushing distally is applied directly to and/or across the radially inner portions.

Example 2

A vascular occluder can comprise a plurality of axially movable fluid permeable flow obstruction portions; wherein the flow obstruction portions are manually compressible against each other in a direction parallel to axis of the blood vessel; wherein the vascular occluder is configured less permeable to blood flowing therethrough in the blood vessel when the flow obstruction portions are pressed tight against each other.

In some embodiments, the plurality of flow obstruction portions includes a fenestrated structure and/or porous material or includes a braided or interwoven structure.

In some embodiments, the vascular occluder further comprising a tension member, wherein the plurality of flow obstruction portions is provided sequentially along a portion of the tension member and extending at least partially transversely thereto. In some embodiments, the tension member passes through a respective lumen of each one of the flow obstruction portions such that one or more of the plurality of flow obstruction portions is movable axially over the tension member relative to remainder of the flow obstruction portions.

Example 3

A vascular occluder can comprise a tension member; and a plurality of flow obstruction portions provided sequentially along a portion of the tension member and extending at least partially transversely thereto, the tension member passes through a respective lumen of each one of the flow obstruction portions such that one or more of the plurality of flow obstruction portions is movable axially over the tension member relative to remainder of the flow obstruction portions.

In some embodiments, the flow obstruction portions are selectively compressible against each other in a direction parallel to the tension member from a more elastically relaxed length to a fixable deployed length, such that radially inner portions thereof are pressed tight against each other.

In some embodiments, the vascular occluder is configured less permeable to blood flowing therethrough in the bodily lumen when the plurality of flow obstruction portions is in the deployed length than when the plurality of flow obstruction portions is in the more elastically relaxed length.

In some embodiments, each one of the flow obstruction portions is partially permeable to blood flowing therethrough and is sized and configured to cover most or all cross section of the bodily lumen portion.

In some embodiments, each one of the flow obstruction portions includes a mesh pattern and/or a braided or interwoven structure.

In some embodiments, the vascular occluder comprising an elongated occluder body comprising a distal body end, a proximal body end and an occluding section extending along a longitudinal axis between the distal body end and the proximal body end, wherein the plurality of flow obstruction portions forms the occluding section.

In some embodiments, the occluding section forms a tubular bellows-like shaped structure comprising a plurality of bellows sections when in an elastically relaxed configuration.

In some embodiments, the occluding section is elastically stretchable longitudinally into a delivery configuration having a delivery length and a delivery diameter, and elastically compressible longitudinally into a deployed configuration having a deployed length smaller than the delivery length and a deployed diameter greater than the delivery diameter.

Example 4

A vascular occluder can comprise an elongated occluder body comprising a distal body end, a proximal body end and an occluding section extending along a longitudinal axis between the distal body end and the proximal body end. In some embodiments, the occluding section, when in an elastically relaxed configuration, forms a tubular bellows-like shaped structure comprising a plurality of bellows sections, and is elastically stretchable longitudinally into a delivery configuration having a delivery length and a delivery diameter, and elastically compressible longitudinally into a deployed configuration having a deployed length smaller than the delivery length and a deployed diameter greater than the delivery diameter.

In some embodiments, the occluding section is configured to lock in the deployed configuration after having been compressed longitudinally into the deployed configuration.

In some embodiments, the occluding section is configured to lock in the deployed configuration when at least one of the bellows sections is held bent towards the longitudinal axis.

In some embodiments, the occluding section is configured to lock in the deployed configuration when at least one of the bellows sections is held bent towards the proximal body end.

In some embodiments, the occluding section is configured to lock in the deployed configuration when at least one of the bellows sections is held deformed such that a radially outer portion thereof is bent towards the longitudinal axis.

In some embodiments, the vascular occluder comprising a length securing member configured to lock the occluding section, selectively or automatically, in the deployed configuration by resisting elongation of the occluding section from the deployed length.

In some embodiments, the vascular occluder further comprising a tension member extending along the occluding section and connected with a distal end thereof to a distal end of the occluding section, the tension member is configured to facilitate selective longitudinal compression of the occluding section.

The In some embodiments, the tension member is connectable to a proximal end of the occluding section when in the deployed configuration for resisting elongation of the occluding section from the deployed length.

In some embodiments, the occluding section encloses a lumen extending along the longitudinal axis, wherein the tension member extends through the lumen.

In some embodiments, the tension member is configured to separate or cut to a predetermined length, optionally when pulled by a force greater than a predetermined tension force.

In some embodiments, the tension member is releasably fixated with the distal end thereof to the distal end of the occluding section, and configured to disconnect from the distal end of the occluding section, optionally when pulled by a force greater than a predetermined tension force.

In some embodiments, the occluding section is configured to reduce blood flow rate passing therethrough along the longitudinal axis when compressing longitudinally to the deployed configuration from a less elastically stressed longitudinally compressed state.

In some embodiments, the occluding section is configured to increase in maximal outer diameter when compressing longitudinally to the deployed configuration from a less elastically stressed longitudinally compressed state.

In some embodiments, the occluding section is configured to increase in elastic resistance to radial compression when compressing longitudinally to the deployed configuration from a less elastically stressed longitudinally compressed state.

In some embodiments, at least one of the plurality of bellows sections extends between respective first and second inward creases, and comprises: a respective frustum-shaped ascending portion extending from the respective first inward crease to a respective outward crease, and a respective frustum-shaped descending portion, extending from the respective outward crease to the respective second inward crease.

In some embodiments, the at least one of the plurality of bellows sections is less permeable adjacent to the respective first inward crease, second inward crease and/or outward crease than to remainder of the respective frustum-shaped ascending portion and/or frustum-shaped descending portion, to blood flow passing therethrough along the longitudinal axis.

In some embodiments, the at least one of the respective frustum-shaped ascending portion and the frustum-shaped descending portion is configured to reduce blood flow permeability therethrough along the longitudinal axis, when the occluding section changes to the deployed configuration.

In some embodiments, in each pair of adjacent bellows sections, comprising of respective first and second bellows sections, the respective second inward crease of the respective first bellows section and the respective first inward crease of the second bellows section are adjoined circumferentially at a mutual curved or bent circumferential inner edge having an inward apex projecting radially-inwardly towards the longitudinal axis.

In some embodiments, the respective outward crease includes a curved or bent circumferential outer edge having an outward apex projecting radially-outwardly from the longitudinal axis.

In some embodiments, a smallest diameter enclosed by the respective second inward crease is greater than a smallest diameter enclosed by the respective first inward crease and smaller than a largest diameter enclosed by the outward crease, in at least one of the plurality of bellows sections.

In some embodiments, in each three sequentially positioned bellows sections of the plurality of bellows sections comprising a respective second bellows section longitudinally positioned between a respective first bellows section and a respective third bellows section, the respective largest diameter enclosed by the respective second bellows section is equal to or greater than the respective largest diameter enclosed by the respective first bellows section and is equal to or smaller than the respective largest diameter enclosed by the respective third bellows section.

In some embodiments, at least some of the plurality of bellows sections vary in enclosed largest diameter.

In some embodiments, the plurality of bellows sections includes at least one larger bellows section having the respective outward crease thereof enclosing a largest diameter greater than diameter of the bodily lumen portion, and at least one smaller bellows section having the respective outward crease thereof enclosing a largest diameter equal to or smaller than diameter of the bodily lumen portion.

In some embodiments, the vascular occluder is configured such that, when the occluding section is in the deployed configuration, the at least one smaller bellows section presses radially outwardly against the larger bellows section.

In some embodiments, at least some of the plurality of bellows sections vary in slant length of the respective frustum-shaped ascending portion and/or frustum-shaped descending portion thereof.

In some embodiments, at least some of the plurality of bellows sections vary in cumulative slant length of the respective frustum-shaped ascending portion and frustum-shaped descending portion thereof.

In some embodiments, in at least one of the plurality of bellows sections the respective frustrum-shaped ascending portion is different in slant length than the respective frustum-shaped descending portion.

In some embodiments, the respective frustum-shaped ascending portion forms an ascending angle with the longitudinal axis and the respective frustum-shaped descending portion forms a descending angle with the longitudinal axis.

In some embodiments, when the occluding section is in the elastically relaxed configuration, the ascending angle is smaller than 90° and the descending angle is greater than 90°.

In some embodiments, when the occluding section is in the deployed configuration, each one of the ascending angle and the descending angle is either greater or smaller than 90°.

In some embodiments, the occluder body is formed of a braided or interwoven sleeve.

In some embodiments, the vascular occluder is configured such that, when the occluding section is in the deployed configuration, radially inner portions of the plurality of bellows sections and/or of distal and proximal body ends are fixedly pressed tight against each other parallel to the longitudinal axis.

In some embodiments, the vascular occluder is configured such that, when the occluding section is in the deployed configuration, the radially inner portions are deformed into a condensed form.

In some embodiments, the vascular occluder is configured such that, when the occluding section is in the deployed configuration, radially outer portions of the plurality of bellows sections, spaced radially outwardly from the radially inner portions, are allowed to shift relative to each other and/or to be arranged with gaps therebetween.

In some embodiments, the delivery length is greater than 10 mm and/or the deployed length is smaller than 6 mm.

In some embodiments, the deployed length is about 50% or less than the delivery length.

In some embodiments, the delivery diameter is smaller than 1.5 mm and the deployed diameter is greater than 3 mm.

Example 5

A method of occluding a blood vessel can comprise: inserting a vascular occluder according to example 4 into the blood vessel proximately to a target wall portion of the blood vessel, wherein the occluding section is held restrained in the delivery configuration; releasing the occluding section in the blood vessel such that the occluding section is allowed to shorten and laterally expand into a less elastically stressed configuration; compressing longitudinally the occluding section into the deployed configuration thereby increasing longitudinal elastic stress of the occluding section relative to the less elastically stressed configuration; and locking the occluding section in the deployed configuration.

In some embodiments, the occluding section is configured to self-lock in the deployed configuration upon compressing longitudinally into the deployed configuration, wherein the compressing longitudinally includes the locking.

In some embodiments, the releasing or the compressing longitudinally includes bending at least one of the bellows sections towards the longitudinal axis, and the compressing longitudinally or locking includes generating continuous internal stresses configured to hold the at least one of the bellows sections bent towards the longitudinal axis, thereby locking the occluding section in the deployed configuration.

In some embodiments, the at least one of the bellows sections is held bent towards the proximal body end.

In some embodiments, the at least one of the bellows sections is held deformed such that a radially outer portion thereof is bent towards the longitudinal axis.

In some embodiments, the vascular occluder comprising a length securing member, wherein the locking includes allowing or selectively applying the length securing member to lock the occluding section in the deployed configuration by resisting lengthwise changes from the deployed length.

In some embodiments, the vascular occluder comprising a tension member extending along the occluding section and connected with a distal end thereof to a distal end of the occluding section, wherein the compressing longitudinally includes applying tension to the tension member.

In some embodiments, the locking includes connecting the tension member to a proximal end of the occluding section when in the deployed configuration, thereby resisting elongation from the deployed length.

In some embodiments, the locking includes or is followed by disjoining or cutting the tension member to a predetermined length by applying tension thereto above a chosen tension force.

In some embodiments, the locking includes or is followed by releasing or disconnecting the tension member from the distal end of the occluding section by applying tension thereto above a chosen tension force.

In some embodiments, the plurality of bellows sections includes at least one larger bellows section and at least one smaller bellows section, wherein the releasing or the compressing longitudinally includes bending the at least one larger bellows section over the at least one smaller bellows section.

In some embodiments, the compressing longitudinally or the locking includes pressing radially outwardly the at least one smaller bellows section against the larger bellows section.

In some embodiments, the compressing longitudinally includes pressing tight radially inner portions of the plurality of bellows sections and/or of the distal and proximal body ends against each other parallelly to the longitudinal axis.

In some embodiments, the pressing tight includes allowing radially outer portions of the plurality of tubular folds spaced radially outwardly from the longitudinal axis to shift relative to each other and/or to arrange with gaps therebetween.

In some embodiments, the pressing tight causes reduced permeability of the occluding section to blood flowing longitudinally therethrough.

In some embodiments, the inserting including ejecting a distal-most one of plurality of bellows sections into a space formed by an aneurism opened to the blood vessel distally to a neck portion of the aneurism adjoining the blood vessel, and ejecting a proximal-most one of the plurality of bellows sections in the blood vessel proximally to the neck portion.

In some embodiments, the locking includes pressing the distal-most one of the plurality of bellows sections against the distal-most one of the plurality of tubular folds across the neck portion.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a'. 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism'. 'a component'. 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '13', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A method of occluding a passage in a body of a live subject, the method comprising:
providing a vascular occluder comprising a braided or interwoven occluding section, the occluding section is configured to form a tubular bellows-like shaped structure comprising a plurality of bellows sections when in an elastically relaxed configuration, and is elastically stretchable longitudinally from the elastically relaxed configuration to a delivery configuration, and elastically compressible longitudinally from the elastically relaxed configuration to a fixed deployed configuration;
inserting the vascular occluder into or through the passage, while maintaining the occluding section in the delivery configuration;
releasing the occluding section in the passage from the delivery configuration such that the occluding section is allowed to shorten and laterally expand into a less elastically stressed configuration;
compressing longitudinally the occluding section into the deployed configuration by increasing longitudinal elastic stress of the occluding section relative to the less elastically stressed configuration, thereby occluding the passage, wherein the compressing includes widening the passage locally with the vascular occluder at least until blood flow rate in the passage reduces by at least 30% of the original blood flow rate; and
locking the occluding section in the deployed configuration.

2. The method according to claim 1, wherein the releasing or the compressing longitudinally includes bending at least one of the bellows sections, and the compressing longitudinally or locking includes generating continuous internal stresses configured to hold the at least one of the bellows sections bent, thereby locking the occluding section in the deployed configuration.

3. The method according to claim 1, wherein the compressing longitudinally includes applying tension to a tension member, and the locking includes fastening a portion of the tension member to the occluder body remotely to the one end of the tension member for preventing or resisting elongation from the deployed length.

4. The method according to claim 3, comprising disjoining or cutting the tension member to a predetermined length, optionally by applying tension thereto above a chosen tension force.

5. The method according to claim 1, wherein the passage is a blood vessel and the occluding affects immediate or gradual cessation of blood flow through the occluding section in the blood vessel.

6. The method according to claim 1, wherein the passage includes an opening in an organ wall separating between distinct organ lumens, wherein the inserting includes passing the occluder body through the opening, and the releasing includes first releasing a distal portion of the occluding section distally to the organ wall and later releasing a proximal portion of the occluding section proximally to the organ wall, such that the compressing occludes the opening.

7. The method according to claim 6, wherein the organ wall is a blood vessel wall and the method is configured to treat vessel wall aneurism or a patent ductus arteriosus; or the organ wall is a septal wall and the method is configured to treat a septal defect such as an atrial septal defect.

8. The method according to claim 1, further comprising:

advancing a catheter enclosing a catheter lumen through a blood vessel, such that a distal opening of the catheter lumen is positioned in the passage; and pushing the vascular occluder with a pusher until protruding at least partially the occluding section in the passage via the distal opening;

wherein the inserting includes the pushing, and/or the compressing includes increasing tension in a tension member sufficiently to compress and lock the occluding section in the deployed configuration.

9. The method according to claim 8, wherein the detaching includes releasing the pusher from being rigidly connected to the occluder body, and/or cutting the tension member distally to the pusher.

\* \* \* \* \*